United States Patent
Jin

(10) Patent No.: US 9,758,836 B2
(45) Date of Patent: Sep. 12, 2017

(54) CITRUS-GREENING (HUANGLONGBING)-INDUCED SMALL RNAS ARE POTENTIAL EARLY DIAGNOSIS MARKERS

(75) Inventor: Hailing Jin, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 305 days.

(21) Appl. No.: 14/003,760

(22) PCT Filed: Mar. 7, 2012

(86) PCT No.: PCT/US2012/028104
§ 371 (c)(1),
(2), (4) Date: Dec. 9, 2013

(87) PCT Pub. No.: WO2012/122290
PCT Pub. Date: Sep. 13, 2012

(65) Prior Publication Data
US 2014/0134266 A1    May 15, 2014

Related U.S. Application Data

(60) Provisional application No. 61/450,050, filed on Mar. 7, 2011.

(51) Int. Cl.
C12Q 1/68 (2006.01)
C12P 19/34 (2006.01)
A01H 3/04 (2006.01)
C12N 15/82 (2006.01)

(52) U.S. Cl.
CPC .............. *C12Q 1/689* (2013.01); *A01H 3/04* (2013.01); *C12N 15/8281* (2013.01); *C12Q 1/6895* (2013.01); *C12N 2310/141* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2010/0257634 A1    10/2010  Bailey et al.
2011/0021463 A1    1/2011   Musson

OTHER PUBLICATIONS

Gong et al; Planta, vol. 230, pp. 671-685, Jul. 2009.*
Albrecht et al., "Gene expression in *Citrus sinensis* (L.) Osbeck following infection with the bacterial pathogen Candidatus Liberibacter asiaticus causing Huanglongbing in Florida"; 2008; Plant Science. vol. 175, pp. 291-306.
Lin et al., "A new diagnostic system for ultra-sensitive and specific detection and quantification of Candidatus Liberibacter asiaticus, the bacterium associated with citrus Hanglonbing"; 2010; *Journal of Microbiological Methods*; vol. 81, pp. 17-25.
International Search Report dated Sep. 25, 2012 in PCT/US2012/028104, filed Mar. 7, 2012, 4 pages.

* cited by examiner

*Primary Examiner* — Jehanne Sitton
(74) *Attorney, Agent, or Firm* — Kilpatrick Townsend & Stockton LLP

(57) ABSTRACT

The present invention provides compositions and methods for detecting *Candidatus Liberibacter* infection and Huanglongbing disease in a citrus plant by detecting the expression of small RNAs such as miRNA and siRNA. The invention also provides methods for treating Huanglongbing disease in a citrus plant by contacting the plant with a phosphorus containing solution.

7 Claims, 5 Drawing Sheets

Figure 1. Expression levels of some conserved miRNA are affected by *Ca.* L. asiaticus infection.

*FIG. 1*

SEQUENCE LISTING

```
<160> NUMBER OF SEQ ID NOS: 101

<210> SEQ ID NO 1
<211> LENGTH: 21
<212> TYPE: DNA
<213> ORGANISM: Artificial Sequence
<220> FEATURE:
<223> OTHER INFORMATION: synthetic citrus miRNA399 small RNA sequence
      with ath-miR399b alignment subject

<400> SEQUENCE: 1
tgccaaagga gagttgccct g                                               21

<210> SEQ ID NO 2
<211> LENGTH: 21
<212> TYPE: DNA
<213> ORGANISM: Artificial Sequence
<220> FEATURE:
<223> OTHER INFORMATION: synthetic citrus miRNA399 small RNA sequence
      with ath-miR399b alignment subject

<400> SEQUENCE: 2
tgccaaagga gagttgccct a                                               21

<210> SEQ ID NO 3
<211> LENGTH: 21
<212> TYPE: DNA
<213> ORGANISM: Artificial Sequence
<220> FEATURE:
<223> OTHER INFORMATION: synthetic citrus miRNA399 small RNA sequence
      with ath-miR399c alignment subject

<400> SEQUENCE: 3
tgccaaagga gcgttgccct g                                               21

<210> SEQ ID NO 4
<211> LENGTH: 21
<212> TYPE: DNA
<213> ORGANISM: Artificial Sequence
<220> FEATURE:
<223> OTHER INFORMATION: synthetic citrus miRNA399 small RNA sequence
      with ath-miR399b alignment subject

<400> SEQUENCE: 4
tgccaaagga gagttgccat g                                               21

<210> SEQ ID NO 5
<211> LENGTH: 21
<212> TYPE: DNA
<213> ORGANISM: Artificial Sequence
```

```
<220> FEATURE:
<223> OTHER INFORMATION: synthetic citrus miRNA399 small RNA sequence
      with ath-miR399c alignment subject

<400> SEQUENCE: 5
tgtcaaagga gagttgccct g                                            21

<210> SEQ ID NO 6
<211> LENGTH: 21
<212> TYPE: DNA
<213> ORGANISM: Artificial Sequence
<220> FEATURE:
<223> OTHER INFORMATION: synthetic citrus miRNA399 small RNA sequence
      with ath-miR399a alignment subject

<400> SEQUENCE: 6
tgccaaagga gaattgccct g                                            21

<210> SEQ ID NO 7
<211> LENGTH: 21
<212> TYPE: DNA
<213> ORGANISM: Artificial Sequence
<220> FEATURE:
<223> OTHER INFORMATION: synthetic citrus miRNA399 small RNA sequence
      with ath-miR399c alignment subject

<400> SEQUENCE: 7
tgctaaagga gagttgccct a                                            21

<210> SEQ ID NO 8
<211> LENGTH: 21
<212> TYPE: DNA
<213> ORGANISM: Artificial Sequence
<220> FEATURE:
<223> OTHER INFORMATION: synthetic citrus miRNA399 small RNA sequence
      with ath-miR399f alignment subject

<400> SEQUENCE: 8
tgccaaagga gatttgcccg g                                            21

<210> SEQ ID NO 9
<211> LENGTH: 21
<212> TYPE: RNA
<213> ORGANISM: Artificial Sequence
<220> FEATURE:
<223> OTHER INFORMATION: synthetic csi-miR399a small RNA sequence

<400> SEQUENCE: 9
ugccaaagga gauugcccg g                                             21

<210> SEQ ID NO 10
<211> LENGTH: 21
<212> TYPE: RNA
<213> ORGANISM: Artificial Sequence
<220> FEATURE:
<223> OTHER INFORMATION: synthetic csi-miR399b small RNA sequence

<400> SEQUENCE: 10
ugccaaagga gaguugcccu a                                            21

<210> SEQ ID NO 11
<211> LENGTH: 21
<212> TYPE: RNA
<213> ORGANISM: Artificial Sequence
<220> FEATURE:
<223> OTHER INFORMATION: synthetic csi-miR399c and csi-miR399e small RNA
      sequence
```

<400> SEQUENCE: 11
ugccaaagga gaauugcccu g                                              21

<210> SEQ ID NO 12
<211> LENGTH: 21
<212> TYPE: RNA
<213> ORGANISM: Artificial Sequence
<220> FEATURE:
<223> OTHER INFORMATION: synthetic csi-miR399d small RNA sequence

<400> SEQUENCE: 12
ugccaaagga gaguugcccu g                                              21

<210> SEQ ID NO 13
<211> LENGTH: 24
<212> TYPE: DNA
<213> ORGANISM: Artificial Sequence
<220> FEATURE:
<223> OTHER INFORMATION: synthetic csi-siR1005 small RNA sequence

<400> SEQUENCE: 13
atagataatg gatcaacggt tata                                           24

<210> SEQ ID NO 14
<211> LENGTH: 21
<212> TYPE: DNA
<213> ORGANISM: Artificial Sequence
<220> FEATURE:
<223> OTHER INFORMATION: synthetic csi-siR1008 small RNA sequence

<400> SEQUENCE: 14
tcgaacaagg taaggatgtc a                                              21

<210> SEQ ID NO 15
<211> LENGTH: 21
<212> TYPE: DNA
<213> ORGANISM: Artificial Sequence
<220> FEATURE:
<223> OTHER INFORMATION: synthetic csi-siR1009 small RNA sequence

<400> SEQUENCE: 15
cttctaataa acatgcatga a                                              21

<210> SEQ ID NO 16
<211> LENGTH: 20
<212> TYPE: RNA
<213> ORGANISM: Artificial Sequence
<220> FEATURE:
<223> OTHER INFORMATION: synthetic citrus miRNA Csi-miR5001 microRNA
      sequence

<400> SEQUENCE: 16
ugaagcugcc agcaugaucu                                                20

<210> SEQ ID NO 17
<211> LENGTH: 19
<212> TYPE: RNA
<213> ORGANISM: Artificial Sequence
<220> FEATURE:
<223> OTHER INFORMATION: synthetic citrus miRNA Csi-miR5001 microRNA
      star

<400> SEQUENCE: 17
aucaucuggc aguuucacc                                                 19

<210> SEQ ID NO 18
<211> LENGTH: 21
<212> TYPE: RNA
<213> ORGANISM: Artificial Sequence
<220> FEATURE:
<223> OTHER INFORMATION: synthetic citrus miRNA Csi-miR5002 microRNA
      sequence

<400> SEQUENCE: 18
uagauaaaga ugagagaaaa a                                           21

<210> SEQ ID NO 19
<211> LENGTH: 21
<212> TYPE: RNA
<213> ORGANISM: Artificial Sequence
<220> FEATURE:
<223> OTHER INFORMATION: synthetic citrus miRNA Csi-miR5002 microRNA
      star

<400> SEQUENCE: 19
uuuucucuua ucguuaucug u                                           21

<210> SEQ ID NO 20
<211> LENGTH: 21
<212> TYPE: RNA
<213> ORGANISM: Artificial Sequence
<220> FEATURE:
<223> OTHER INFORMATION: synthetic citrus miRNA Csi-miR5003 microRNA
      sequence

<400> SEQUENCE: 20
uuuguugcau gaugcugaua a                                           21

<210> SEQ ID NO 21
<211> LENGTH: 21
<212> TYPE: RNA
<213> ORGANISM: Artificial Sequence
<220> FEATURE:
<223> OTHER INFORMATION: synthetic citrus miRNA Csi-miR5003 microRNA
      star

<400> SEQUENCE: 21
cuacccgcau caugcaacaa a                                           21

<210> SEQ ID NO 22
<211> LENGTH: 24
<212> TYPE: RNA
<213> ORGANISM: Artificial Sequence
<220> FEATURE:
<223> OTHER INFORMATION: synthetic citrus miRNA Csi-miR5004 microRNA
      sequence

<400> SEQUENCE: 22
aguguuaggu guagagaagc acga                                        24

<210> SEQ ID NO 23
<211> LENGTH: 24
<212> TYPE: RNA
<213> ORGANISM: Artificial Sequence
<220> FEATURE:
<223> OTHER INFORMATION: synthetic citrus miRNA Csi-miR5004 microRNA
      star

<400> SEQUENCE: 23
ucucguacuu cucuucacca agca                                        24

<210> SEQ ID NO 24
<211> LENGTH: 20
<212> TYPE: RNA
<213> ORGANISM: Artificial Sequence
<220> FEATURE:
<223> OTHER INFORMATION: synthetic citrus miRNA Csi-miR5005 microRNA
      sequence

<400> SEQUENCE: 24
auucgggacg aguuuacaac                                           20

<210> SEQ ID NO 25
<211> LENGTH: 20
<212> TYPE: RNA
<213> ORGANISM: Artificial Sequence
<220> FEATURE:
<223> OTHER INFORMATION: synthetic citrus miRNA Csi-miR5005 microRNA
      star

<400> SEQUENCE: 25
cguaaacucg ucucguacuu                                           20

<210> SEQ ID NO 26
<211> LENGTH: 21
<212> TYPE: RNA
<213> ORGANISM: Artificial Sequence
<220> FEATURE:
<223> OTHER INFORMATION: synthetic citrus miRNA Csi-miR5006 microRNA
      sequence

<400> SEQUENCE: 26
aauggcugga uccagcugug g                                         21

<210> SEQ ID NO 27
<211> LENGTH: 21
<212> TYPE: RNA
<213> ORGANISM: Artificial Sequence
<220> FEATURE:
<223> OTHER INFORMATION: synthetic citrus miRNA Csi-miR5006 microRNA
      star

<400> SEQUENCE: 27
acaauuggau uuagccauua a                                         21

<210> SEQ ID NO 28
<211> LENGTH: 19
<212> TYPE: RNA
<213> ORGANISM: Artificial Sequence
<220> FEATURE:
<223> OTHER INFORMATION: synthetic citrus miRNA Csi-miR5007 microRNA
      sequence

<400> SEQUENCE: 28
augccguauc acgugggag                                            19

<210> SEQ ID NO 29
<211> LENGTH: 19
<212> TYPE: RNA
<213> ORGANISM: Artificial Sequence
<220> FEATURE:
<223> OTHER INFORMATION: synthetic citrus miRNA Csi-miR5007 microRNA
      star

<400> SEQUENCE: 29
cccacuugau gugucauuc                                            19

<210> SEQ ID NO 30

```
<211> LENGTH: 21
<212> TYPE: RNA
<213> ORGANISM: Artificial Sequence
<220> FEATURE:
<223> OTHER INFORMATION: synthetic citrus miRNA Csi-miR5008 microRNA
      sequence

<400> SEQUENCE: 30
uuugaugccu ucuuuagucg c                                              21

<210> SEQ ID NO 31
<211> LENGTH: 20
<212> TYPE: RNA
<213> ORGANISM: Artificial Sequence
<220> FEATURE:
<223> OTHER INFORMATION: synthetic citrus miRNA Csi-miR5008 microRNA
      star

<400> SEQUENCE: 31
gauuaaggag aguuuucagu                                                20

<210> SEQ ID NO 32
<211> LENGTH: 19
<212> TYPE: DNA
<213> ORGANISM: Artificial Sequence
<220> FEATURE:
<223> OTHER INFORMATION: synthetic citrus miRNA Csi-miR5009 microRNA
      sequence

<400> SEQUENCE: 32
gacagaagag agtgagcac                                                 19

<210> SEQ ID NO 33
<211> LENGTH: 20
<212> TYPE: RNA
<213> ORGANISM: Artificial Sequence
<220> FEATURE:
<223> OTHER INFORMATION: synthetic citrus miRNA Csi-miR5009 microRNA
      star

<400> SEQUENCE: 33
gcucgcuccu cuucugucag                                                20

<210> SEQ ID NO 34
<211> LENGTH: 20
<212> TYPE: RNA
<213> ORGANISM: Artificial Sequence
<220> FEATURE:
<223> OTHER INFORMATION: synthetic citrus miRNA Csi-miR5010 microRNA
      sequence

<400> SEQUENCE: 34
guauauaucu ugcaugcaug                                                20

<210> SEQ ID NO 35
<211> LENGTH: 19
<212> TYPE: RNA
<213> ORGANISM: Artificial Sequence
<220> FEATURE:
<223> OTHER INFORMATION: synthetic citrus miRNA Csi-miR5010 microRNA
      star

<400> SEQUENCE: 35
guauguaaga uacaucccc                                                 19

<210> SEQ ID NO 36
<211> LENGTH: 20
```

-continued

```
<212> TYPE: RNA
<213> ORGANISM: Artificial Sequence
<220> FEATURE:
<223> OTHER INFORMATION: synthetic citrus miRNA Csi-miR5011 microRNA
      sequence

<400> SEQUENCE: 36
uuucucuuau cguuaucugu                                             20

<210> SEQ ID NO 37
<211> LENGTH: 21
<212> TYPE: RNA
<213> ORGANISM: Artificial Sequence
<220> FEATURE:
<223> OTHER INFORMATION: synthetic citrus miRNA Csi-miR5011 microRNA
      star

<400> SEQUENCE: 37
uagauaaaga ugagagaaaa a                                           21

<210> SEQ ID NO 38
<211> LENGTH: 22
<212> TYPE: RNA
<213> ORGANISM: Artificial Sequence
<220> FEATURE:
<223> OTHER INFORMATION: synthetic citrus miRNA Csi-miR5012 microRNA
      sequence

<400> SEQUENCE: 38
uuguuguuga guguguaugu ua                                          22

<210> SEQ ID NO 39
<211> LENGTH: 22
<212> TYPE: RNA
<213> ORGANISM: Artificial Sequence
<220> FEATURE:
<223> OTHER INFORMATION: synthetic citrus miRNA Csi-miR5012 microRNA
      star

<400> SEQUENCE: 39
acauaaauac uuaauaauaa uc                                          22

<210> SEQ ID NO 40
<211> LENGTH: 21
<212> TYPE: RNA
<213> ORGANISM: Artificial Sequence
<220> FEATURE:
<223> OTHER INFORMATION: synthetic citrus miRNA Csi-miR5013 microRNA
      sequence

<400> SEQUENCE: 40
ucguccuucu cucauauuuu u                                           21

<210> SEQ ID NO 41
<211> LENGTH: 20
<212> TYPE: RNA
<213> ORGANISM: Artificial Sequence
<220> FEATURE:
<223> OTHER INFORMATION: synthetic citrus miRNA Csi-miR5013 microRNA
      star

<400> SEQUENCE: 41
agagugggug ggguggagagg                                            20

<210> SEQ ID NO 42
<211> LENGTH: 21
<212> TYPE: DNA
```

```
<213> ORGANISM: Artificial Sequence
<220> FEATURE:
<223> OTHER INFORMATION: synthetic HLB induced citrus siRNA

<400> SEQUENCE: 42
ttccagatag aaggccactc a                                              21

<210> SEQ ID NO 43
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 43
ttccaccaat cgatcaggat a                                              21

<210> SEQ ID NO 44
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 44
gcgtatgagg agccatgcat a                                              21

<210> SEQ ID NO 45
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 45
cttggattta tgaaagacga a                                              21

<210> SEQ ID NO 46
<211> LENGTH: 23
<212> TYPE: DNA
<213> ORGANISM: Artificial Sequence
<220> FEATURE:
<223> OTHER INFORMATION: synthetic HLB induced citrus siRNA

<400> SEQUENCE: 46
ggcagggcta gtgactggag tga                                            23

<210> SEQ ID NO 47
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 47
acaggccgca aacatttttcc t                                             21

<210> SEQ ID NO 48
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 48
acagaccgca caccttttct t                                              21
```

-continued

<210> SEQ ID NO 49
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 49
attaggagct aaaattgttg t                                              21

<210> SEQ ID NO 50
<211> LENGTH: 24
<212> TYPE: DNA
<213> ORGANISM: Artificial Sequence
<220> FEATURE:
<223> OTHER INFORMATION: synthetic HLB induced citrus siRNA

<400> SEQUENCE: 50
acgaaatgtg agtagagtgg acag                                           24

<210> SEQ ID NO 51
<211> LENGTH: 20
<212> TYPE: DNA
<213> ORGANISM: Artificial Sequence
<220> FEATURE:
<223> OTHER INFORMATION: synthetic HLB induced citrus siRNA

<400> SEQUENCE: 51
ttccaaaggg atcgcattga                                                20

<210> SEQ ID NO 52
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 52
tcatttaagg gtttcgtgtt c                                              21

<210> SEQ ID NO 53
<211> LENGTH: 24
<212> TYPE: DNA
<213> ORGANISM: Artificial Sequence
<220> FEATURE:
<223> OTHER INFORMATION: synthetic HLB induced citrus siRNA

<400> SEQUENCE: 53
acgctcggac gaagcacata gatg                                           24

<210> SEQ ID NO 54
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 54
tatgggattt acctcggcaa a                                              21

<210> SEQ ID NO 55
<211> LENGTH: 21
<212> TYPE: DNA
<213> ORGANISM: Artificial Sequence
<220> FEATURE:

-continued

<223> OTHER INFORMATION: synthetic HLB induced citrus siRNA

<400> SEQUENCE: 55
tgtgtggatg aataagattt c							21

<210> SEQ ID NO 56
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 56
tatctggata aaaggctacc c							21

<210> SEQ ID NO 57
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 57
tcatggataa ggtcatgcat t							21

<210> SEQ ID NO 58
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 58
aaaaacttgg aagcgttgga t							21

<210> SEQ ID NO 59
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 59
tcctgccggg ttgcataatc a							21

<210> SEQ ID NO 60
<211> LENGTH: 24
<212> TYPE: DNA
<213> ORGANISM: Artificial Sequence
<220> FEATURE:
<223> OTHER INFORMATION: synthetic HLB induced citrus siRNA

<400> SEQUENCE: 60
atagataatg gatcaacggt tata						24

<210> SEQ ID NO 61
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 61
tcatggataa ggtcatgcat c							21

<210> SEQ ID NO 62
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 62
ctgaaagctg aggttgtcct t 21

<210> SEQ ID NO 63
<211> LENGTH: 24
<212> TYPE: DNA
<213> ORGANISM: Artificial Sequence
<220> FEATURE:
<223> OTHER INFORMATION: synthetic HLB induced citrus siRNA

<400> SEQUENCE: 63
agtgtcaaaa agagcaatgg cgtc 24

<210> SEQ ID NO 64
<211> LENGTH: 24
<212> TYPE: DNA
<213> ORGANISM: Artificial Sequence
<220> FEATURE:
<223> OTHER INFORMATION: synthetic HLB induced citrus siRNA

<400> SEQUENCE: 64
aatccttgga ttaggagtgt ggag 24

<210> SEQ ID NO 65
<211> LENGTH: 24
<212> TYPE: DNA
<213> ORGANISM: Artificial Sequence
<220> FEATURE:
<223> OTHER INFORMATION: synthetic HLB induced citrus siRNA

<400> SEQUENCE: 65
atcaataaat caggattggc ggaa 24

<210> SEQ ID NO 66
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 66
cgttagggag tccggagacg t 21

<210> SEQ ID NO 67
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 67
gaataagaca tggagttgga a 21

<210> SEQ ID NO 68
<211> LENGTH: 24
<212> TYPE: DNA
<213> ORGANISM: Artificial Sequence
<220> FEATURE:
<223> OTHER INFORMATION: synthetic HLB induced citrus siRNA

```
<400> SEQUENCE: 68
aggaaatgga cgatacggac gcat                                          24

<210> SEQ ID NO 69
<211> LENGTH: 23
<212> TYPE: DNA
<213> ORGANISM: Artificial Sequence
<220> FEATURE:
<223> OTHER INFORMATION: synthetic HLB induced citrus siRNA

<400> SEQUENCE: 69
tcaagtgagg ttcggtcttt gaa                                           23

<210> SEQ ID NO 70
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 70
taatcgtggg agacgaagct g                                             21

<210> SEQ ID NO 71
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 71
cgaaggtccg aggtcgaggt t                                             21

<210> SEQ ID NO 72
<211> LENGTH: 24
<212> TYPE: DNA
<213> ORGANISM: Artificial Sequence
<220> FEATURE:
<223> OTHER INFORMATION: synthetic HLB induced citrus siRNA

<400> SEQUENCE: 72
aggtttgggc ttgttgcaag taga                                          24

<210> SEQ ID NO 73
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 73
tccgggcgga agacattgtc a                                             21

<210> SEQ ID NO 74
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 74
aacggaaaga acacaacacg g                                             21

<210> SEQ ID NO 75
<211> LENGTH: 21
```

```
<212> TYPE: DNA
<213> ORGANISM: Artificial Sequence
<220> FEATURE:
<223> OTHER INFORMATION: synthetic HLB induced citrus siRNA

<400> SEQUENCE: 75
tgttagcttt ctcggacgca g                                           21

<210> SEQ ID NO 76
<211> LENGTH: 22
<212> TYPE: DNA
<213> ORGANISM: Artificial Sequence
<220> FEATURE:
<223> OTHER INFORMATION: synthetic HLB induced citrus siRNA

<400> SEQUENCE: 76
tcaagtgagg ttctgtcttt ga                                          22

<210> SEQ ID NO 77
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 77
aaagcaacga ttgtatggcc a                                           21

<210> SEQ ID NO 78
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 78
tcaagtgagg ttcggtcttg a                                           21

<210> SEQ ID NO 79
<211> LENGTH: 24
<212> TYPE: DNA
<213> ORGANISM: Artificial Sequence
<220> FEATURE:
<223> OTHER INFORMATION: synthetic HLB induced citrus siRNA

<400> SEQUENCE: 79
gaatgtggaa ttaagcgcac caaa                                        24

<210> SEQ ID NO 80
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 80
tcgaacaagg taaggatgtc a                                           21

<210> SEQ ID NO 81
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 81
```
ctggatgcaa ctgtggtacg g                                              21

<210> SEQ ID NO 82
<211> LENGTH: 21
<212> TYPE: DNA
<213> ORGANISM: Artificial Sequence
<220> FEATURE:
<223> OTHER INFORMATION: synthetic HLB induced citrus siRNA

<400> SEQUENCE: 82
ggtgcttccg gatctcagga t                                              21

<210> SEQ ID NO 83
<211> LENGTH: 18
<212> TYPE: DNA
<213> ORGANISM: Artificial Sequence
<220> FEATURE:
<223> OTHER INFORMATION: synthetic HLB induced citrus siRNA

<400> SEQUENCE: 83
cacatgggtt agtcgatc                                                  18

<210> SEQ ID NO 84
<211> LENGTH: 1066
<212> TYPE: DNA
<213> ORGANISM: Citrus sinensis
<220> FEATURE:
<223> OTHER INFORMATION: citrus homolog of ubiquitin conjugating enzyme
      E2 (UBC)

<400> SEQUENCE: 84
cacgcgtccg ggtgaaaaga gcttgggtga agaaggtcag caagaatgga gcattctaga    60
gaaatccctt cctgaaacaa tctatgtccg catcttcgag gatagggtgg atctcatacg   120
ggcagccatt gttggtgcaa agggaactcc ctatcacgac gggctgttct tctttgacat   180
ctttcttcct ccagagtatc ctcatgagcc gcctttagta cactatattt ctggtggact   240
ccgtgtgaac cctaacttgt atgagtccgg aaaggtctgt ctcagcctcc tcaatacttg   300
gacgggttca ggcactgaag tatgaatccc aggggctcc acgattcttc aagttcttct   360
ctccctccaa gctcttgtgc ttaatgagaa accttatttc aacgaggctg atatgataa    420
gcagatagga agagctgagg gagagaaaaa ctcagtaagc tacaatgaaa atgcattcct   480
tgtgacttgc aagtccatgc tttacctact tcacaagcca cccaagcatt ttaaggagct   540
tgtggaggag cacttcagtc aacgctgcaa atacatttta ttggcttgta aggcatacat   600
ggaaggagct gcagtaggaa ctccctctgg atgcaaagaa aatggagaaa attccaacgg   660
atgttcagtg ggcttcaaaa tcatgcttgc ctaagttatt tccaaagctt gtgcaggcct   720
tttctagtaa gggaatcgat tgcaaccaat ttattgagcc tgaaaactga aaatgaatg    780
cccttcacgg gttcaaataa ttaaaagaac tcgcatttac cttatgaaca cattcctatc   840
gtgtgaatta aaatgtaaaa taacaaaata tgcttgtgtt tcttctgtgc tctgtttaca   900
tgggcgttga acttgtatta taagattggt tgaataagcg tttgctgctg taatatatgg   960
tgtatcacaa tgtacaataa tgaagaaaca atggtcgcag tggtgtgcct taagatcttt  1020
gtaaaaaaaa aaaaaaaaaa aaaaaaaaaa aaaaaaaaaa aaaaaa                  1066

<210> SEQ ID NO 85
<211> LENGTH: 50
<212> TYPE: DNA
<213> ORGANISM: Artificial Sequence
<220> FEATURE:

<223> OTHER INFORMATION: synthetic miR399b RT primer

<400> SEQUENCE: 85
gtcgtatcca gtgcagggtc cgaggtattc gcactggata cgacatgggc    50

<210> SEQ ID NO 86
<211> LENGTH: 22
<212> TYPE: DNA
<213> ORGANISM: Artificial Sequence
<220> FEATURE:
<223> OTHER INFORMATION: synthetic PCR primer miR399b RT-F

<400> SEQUENCE: 86
gcggcggtgc caaaggagag tt    22

<210> SEQ ID NO 87
<211> LENGTH: 16
<212> TYPE: DNA
<213> ORGANISM: Artificial Sequence
<220> FEATURE:
<223> OTHER INFORMATION: synthetic PCR primer miR399b RT-R

<400> SEQUENCE: 87
gtgcagggtc cgaggt    16

<210> SEQ ID NO 88
<211> LENGTH: 50
<212> TYPE: DNA
<213> ORGANISM: Artificial Sequence
<220> FEATURE:
<223> OTHER INFORMATION: synthetic csi-siR1005 RT primer

<400> SEQUENCE: 88
gtcgtatcca gtgcagggtc cgaggtattc gcactggata cgacgttata    50

<210> SEQ ID NO 89
<211> LENGTH: 25
<212> TYPE: DNA
<213> ORGANISM: Artificial Sequence
<220> FEATURE:
<223> OTHER INFORMATION: synthetic PCR primer csi-siR1005 RT-F

<400> SEQUENCE: 89
gcggcggata gataatggat caacg    25

<210> SEQ ID NO 90
<211> LENGTH: 16
<212> TYPE: DNA
<213> ORGANISM: Artificial Sequence
<220> FEATURE:
<223> OTHER INFORMATION: synthetic PCR primer csi-siR1005 RT-R

<400> SEQUENCE: 90
gtgcagggtc cgaggt    16

<210> SEQ ID NO 91
<211> LENGTH: 50
<212> TYPE: DNA
<213> ORGANISM: Artificial Sequence
<220> FEATURE:
<223> OTHER INFORMATION: synthetic csi-siR1008 RT primer

<400> SEQUENCE: 91
gtcgtatcca gtgcagggtc cgaggtattc gcactggata cgacatgtca    50

```
<210> SEQ ID NO 92
<211> LENGTH: 22
<212> TYPE: DNA
<213> ORGANISM: Artificial Sequence
<220> FEATURE:
<223> OTHER INFORMATION: synthetic PCR primer csi-siR1008 RT-F

<400> SEQUENCE: 92
gcggcggtcg aacaaggtaa gg                                              22

<210> SEQ ID NO 93
<211> LENGTH: 16
<212> TYPE: DNA
<213> ORGANISM: Artificial Sequence
<220> FEATURE:
<223> OTHER INFORMATION: synthetic PCR primer csi-siR1008 RT-R

<400> SEQUENCE: 93
gtgcagggtc cgaggt                                                     16

<210> SEQ ID NO 94
<211> LENGTH: 50
<212> TYPE: DNA
<213> ORGANISM: Artificial Sequence
<220> FEATURE:
<223> OTHER INFORMATION: synthetic csi-siR1009 RT primer

<400> SEQUENCE: 94
gtcgtatcca gtgcagggtc cgaggtattc gcactggata cgaccatgaa                50

<210> SEQ ID NO 95
<211> LENGTH: 22
<212> TYPE: DNA
<213> ORGANISM: Artificial Sequence
<220> FEATURE:
<223> OTHER INFORMATION: synthetic PCR primer csi-siR1009 RT-F

<400> SEQUENCE: 95
gcggcggctt ctaataaaca tg                                              22

<210> SEQ ID NO 96
<211> LENGTH: 16
<212> TYPE: DNA
<213> ORGANISM: Artificial Sequence
<220> FEATURE:
<223> OTHER INFORMATION: synthetic PCR primer csi-siR1009 RT-R

<400> SEQUENCE: 96
gtgcagggtc cgaggt                                                     16

<210> SEQ ID NO 97
<211> LENGTH: 28
<212> TYPE: RNA
<213> ORGANISM: Artificial Sequence
<220> FEATURE:
<223> OTHER INFORMATION: synthetic 5' adaptor

<400> SEQUENCE: 97
guucagaguu cuacaguccg acgaucag                                        28

<210> SEQ ID NO 98
<211> LENGTH: 21
<212> TYPE: RNA
<213> ORGANISM: Artificial Sequence
<220> FEATURE:
<223> OTHER INFORMATION: synthetic 3' adaptor
```

```
<400> SEQUENCE: 98
ucguaugccg ucuucugcuu g                                              21

<210> SEQ ID NO 99
<211> LENGTH: 21
<212> TYPE: DNA
<213> ORGANISM: Artificial Sequence
<220> FEATURE:
<223> OTHER INFORMATION: synthetic miRNA399 consensus sequence

<400> SEQUENCE: 99
tgyyaaagga gmdttgccmk r                                              21

<210> SEQ ID NO 100
<211> LENGTH: 33
<212> TYPE: DNA
<213> ORGANISM: Artificial Sequence
<220> FEATURE:
<223> OTHER INFORMATION: synthetic csi-siR1008 detected sequence with
      varying 5' and 3' ends

<400> SEQUENCE: 100
ccttgttcga acaaggtaag gatgtcattc ttt                                 33

<210> SEQ ID NO 101
<211> LENGTH: 30
<212> TYPE: DNA
<213> ORGANISM: Artificial Sequence
<220> FEATURE:
<223> OTHER INFORMATION: synthetic csi-siR1009 detected sequence with
      varying 5' and 3' ends

<400> SEQUENCE: 101
cgtcttctaa taaacatgca tgaacttatt                                     30
```

CITRUS-GREENING (HUANGLONGBING)-INDUCED SMALL RNAS ARE POTENTIAL EARLY DIAGNOSIS MARKERS

CROSS-REFERENCES TO RELATED APPLICATIONS

The present application claims benefit of priority to International Application No. PCT/US2012/028104, filed Mar. 7, 2012, and U.S. Provisional Patent Application No. 61/450,050, filed Mar. 7, 2011, the contents of each of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 887952-21110US-Substitute-Sequence-Listing.TXT, created on Sep. 24, 2013, 24,576 bytes, machine format IBM-PC, MS-Windows operating system, is hereby incorporated by reference in its entirety for all purposes.

BACKGROUND OF THE INVENTION

Citrus greening, also called Huanglongbing or yellow dragon disease, is a disease of citrus. This bacterial disease is thought to have originated in China in the early 1900's. The disease is primarily spread by two species of psyllid insects. One species, the Asian citrus psyllid, *Diaphorina citri*, has been present in Florida since 1998. The bacteria itself is not harmful to humans but the disease is damaging to the citrus crops. There are three strains of the bacteria: an Asian version, an African version, and a recently described American strain discovered in Brazil.

The Asian strain, *Candidatus Liberibacter asiaticus* (*Ca. L.*, Las), was found in Florida in early September, 2005. As a result, citrus greening disease is becoming a major threat to the U.S. citrus industry. Other than tree removal, there has been no known effective control once a tree is infected and there has been no known cure for the disease. Infected trees may produce misshapen, unmarketable, bitter fruit, or no fruit. Citrus greening reduces the quantity and quality of citrus fruits, eventually rendering infected trees useless. In areas of the world affected by citrus greening the average productive lifespan of citrus trees has dropped from 50 or more years to 15 or less. The trees in the orchards usually die 3-5 years after becoming infected and require removal and replanting. An infected tree produces fruit that is unsuitable for sale as fresh fruit or for juice.

Citrus plants infected by the citrus greening bacteria may not show symptoms for years following infection. Initial symptoms frequently include the appearance of yellow shoots on a tree. As the bacteria grow and move within the tree, the entire canopy progressively develops a yellow color.

The most characteristic symptoms of citrus greening are a blotchy leaf mottle and vein yellowing that develop on leaves attached to shoots, providing the overall yellow appearance. These foliar symptoms may superficially resemble a zinc deficiency although the green and yellow contrast is not as vivid with greening as it is with zinc deficiency or another disease, citrus variegated chlorosis. Leaves with citrus greening have a mottled appearance that differs from nutrition-related mottling in that greening-induced mottling usually crosses leaf veins. Nutrition related mottles usually are found between or along leaf veins and leaves may be small and upright.

Fruit from diseased trees are small, often misshapen, and typically some green color remains on ripened fruit. On Mandarin orange, fruit may develop an uneven ripening such that they appear half orange and half yellow. This symptom is the origin of the common name "greening." Yields are almost minimal, and any developed fruit is rendered worthless due to small size, poor color, and bad taste.

BRIEF SUMMARY OF THE INVENTION

The present disclosure provides compositions and methods for determining if a citrus plant has Huanglongbing (HLB) disease or is infected with *Candidatus Liberibacter* (*Ca. L.*). In one aspect, HLB disease or infection with *Ca. L.* is detected by detecting the expression level of a small RNA, such as a micro RNA or small interfering RNA, in the plant, and comparing the level of the small RNA to the level detected in a control, non-infected, plant. Thus, in some embodiments, a method for detection of HLB disease or *Ca. L. asiaticus*-infection in a citrus plant is provided, the method comprising detecting in a sample from the citrus plant the level of expression of one or more RNAs selected from the group consisting of miRNA399, siRNA1005, siRNA1008 or siRNA1009, wherein increased expression of the one or more RNAs compared to expression of the RNA in a non-infected healthy plant indicates the presence of *Ca. L. asiaticus*-infection.

In some embodiments, miRNA399 comprises the consensus sequence TG $X_1$ $X_2$ AAAGGAG $X_3$ $X_4$ TTGCC $X_5$ $X_6$ $X_2$, where $X_1$ is C or T, $X_2$ is C or T, $X_3$ is A or C, $X_4$ is G, T, or A, $X_5$ is C or A, $X_6$ is T or G, and $X_2$ is A or G (SEQ ID NO:99).

In some embodiments, miRNA399 comprises a sequence that is substantially identical to (e.g., at least 80%, 85%, 90%, or 95% identical to) a sequence selected from TGC-CAAAGGAGAGTTGCCCTG (SEQ ID NO:1), TGC-CAAAGGAGAGTTGCCCTA (SEQ ID NO:2), TGC-CAAAGGAGATTTGCCCGG (SEQ ID NO:8), and TGCCAAAGGAGAATTGCCCTG (SEQ ID NO:6).

In some embodiments, miRNA399 comprises a sequence that is substantially identical to (e.g., at least 80%, 85%, 90%, or 95% identical to) a sequence selected from UGC-CAAAGGAGAUUUGCCCGG (SEQ ID NO:9), UGC-CAAAGGAGAGUUGCCCUA (SEQ ID NO:10), UGC-CAAAGGAGAAUUGCCCUG (SEQ ID NO:11), and UGCCAAAGGAGAGUUGCCCUG (SEQ ID NO:12).

In some embodiments, the siRNA1005 comprises a sequence that is substantially identical to (e.g., at least 80%, 85%, 90%, or 95% identical to) the sequence ATAGA-TAATGGATCAACGGTTATA (SEQ ID NO:13). In some embodiments, the siRNA1008 comprises a sequence that is substantially identical to (e.g., at least 80%, 85%, 90%, or 95% identical to) the sequence TCGAACAAGG-TAAGGATGTCA (SEQ ID NO:14). In some embodiments, the siRNA1009 comprises a sequence that is substantially identical to (e.g., at least 80%, 85%, 90%, or 95% identical to) the sequence CTTCTAATAAACATGCATGAA (SEQ ID NO:15).

In some embodiments, the method further comprises detecting the mRNA of a ubiquitin-conjugating enzyme gene. In one embodiment, the ubiquitin-conjugating enzyme is ubiquitin-conjugating enzyme E2 (UBC). In one embodiment, the UBC gene or mRNA comprises a sequence that is substantially identical to (e.g., at least 80%, 85%, 90%, or 95% identical to) SEQ ID NO:84.

In some embodiments, the method further comprises measuring phosphate levels in the plant.

In one embodiment, the method further comprises contacting the plant with phosphorus oxyanions if the plant is infected with Ca. L. The phosphorus oxyanions can be present in a solution.

In another aspect, the disclosure provides a method for treating a plant having HLB disease. In one embodiment, the method comprises contacting a plant having HLB disease or infected with Ca. L. with phosphite or phosphorus oxyanions in sufficient amount to ameliorate the symptoms of HLB disease in the plant. In one embodiment, the phosphite or phosphorus oxyanions are in a solution. Contacting the infected plant with phosphorus oxyanions stimulates phosphate uptake in the plant by suppressing UBC mRNA or UBC protein expression and/or activity, which in turn induces the expression of phosphate transporters in the plant, thereby ameliorating symptoms of HLB disease.

In another aspect, the disclosure provides a kit for detection of HLB disease or Ca. L. infection. In some embodiments, the kit comprises one or more agents that specifically detects a small RNA, including miRNA399, miRNA159, siRNA1005, siRNA1008 or siRNA1009.

Definitions

As used herein and in the appended claims, the singular forms "a," "and," and "the" include plural referents unless the context clearly dictates otherwise. Thus, for example, reference to "a plant" includes a plurality of such plants and reference to "the tree" includes reference to one or more trees known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 60% sequence identity with a reference sequence. Alternatively, percent identity can be any integer from 60% to 100%. Some embodiments include at least: 60%, 65%, 70%, 75%, 80%, 85%, 90%, 91%, 92%, 93%, 94% 95%, 96%, 97%, 98%, or 99%, compared to a reference sequence using the programs described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appi. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is the only natural codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the methods of the invention includes angiosperms (monocotyledonous and dicotyledonous plants), gymnosperms, ferns, bryophytes, and multicellular and unicellular algae. It includes plants of a variety of ploidy levels, including aneuploid, polyploid, diploid, haploid, and hemizygous.

As used herein, the term "transgenic" describes a non-naturally occurring plant that contains a genome modified by man, wherein the plant includes in its genome an exogenous nucleic acid molecule, which can be derived from the same or a different plant species. The exogenous nucleic acid molecule can be a gene regulatory element such as a promoter, enhancer, or other regulatory element, or can contain a coding sequence, which can be linked to a heterologous gene regulatory element. Transgenic plants that arise from sexual cross or by selfing are descendants of such a plant and are also considered "transgenic.".

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct that, when introduced into a host cell, results in transcription and/or translation of an RNA or polypeptide, respectively. In the case of both expression of transgenes and suppression of endogenous genes or regulatory elements (e.g., by small RNAs) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence.

BRIEF DESCRIPTION OF THE DRAWINGS

FIG. 1 shows expression levels of some conserved citrus miRNAs are affected by Las infection. Relative expression levels of some conserved citrus miRNAs were examined at 10 wpi (a) and 14 wpi (b). Expression levels are presented as reads in Las-treated samples over corresponding untreated samples. "+1" indicates a 2-fold induction; "−1" indicates a 2-fold reduction; HLB: Las-infected; wpi: weeks post inoculation. Red bar highlights miR399, which is involved in citrus Pi accumulation. The miRNA IDs are listed at the left side.

DETAILED DESCRIPTION OF THE INVENTION

Introduction

Figure 2:
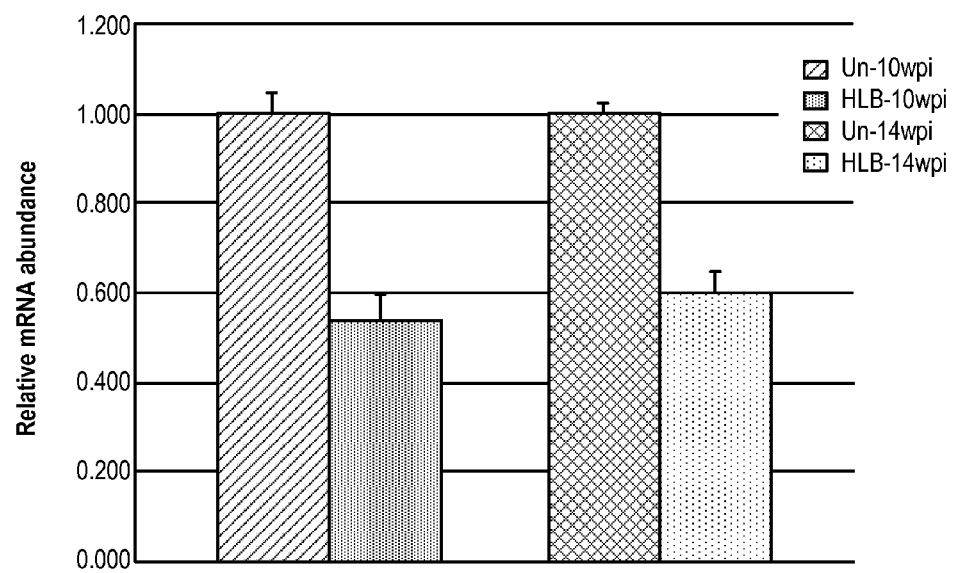
FIG. 2 is a graph showing *Ca. L. asiaticus*-induced miR399 down-regulates its target, a E2-conjugating enzyme gene UBC. UBC mRNA was measured by real-time RT-PCR and actin was used as an internal control. Similar results were obtained from two biological replicates.
Figure 3:
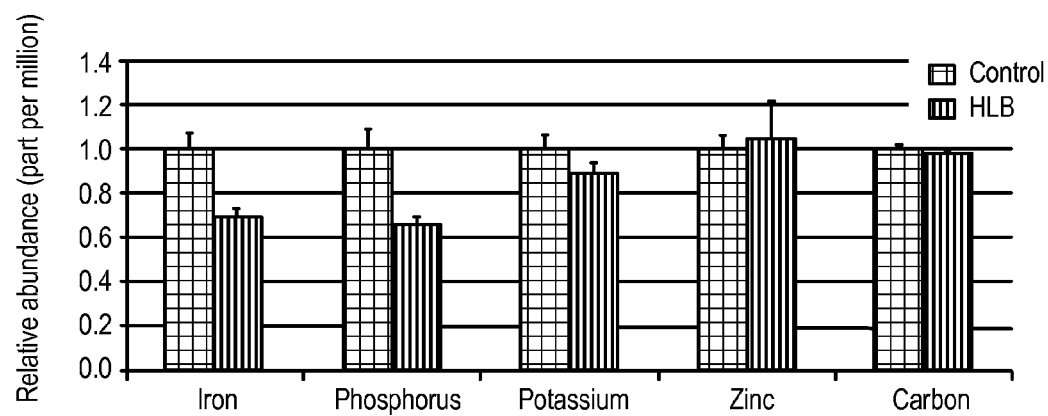
FIG. 3 shows that Las infection causes citrus phosphorus and iron deficiency. 15-20 leaves from both untreated and Las-treated trees were collected. For the treated plants, both asymptomatic and symptomatic leaves were collected. For symptomatic leaves a combination of blotchy mottled and small chlorotic leaves of different ages was collected. For asymptomatic and control leaves, a combination of older and younger leaves was collected (if possible). Amount of iron, phosphorus, potassium, zinc, and carbon was examined (mean±SE). Amount of each element in untreated samples was assigned to 1. Experiments were repeated for 2 times with similar results.

Citrus greening or "Huanglongbing" (HLB), caused by bacteria *Candidatus Liberobacter*, is one of the most destructive diseases of citrus. *Candidatus Liberibacter* (*Ca. Liberibacter* or *Ca. L.*) is a Gram negative bacterial pathogen restricted to the phloem. The uneven distribution within trees and the latency of detectable symptoms make detection and confirmation of asymptomatic infections very difficult. Therefore, developing early diagnosis biomarkers and effective reagents is an urgent need for the citrus industry, especially for those in the threatened but un-infected regions, such as California. The recent detection of Psyllids (the insect vector for pathogen infection) at the California-Mexico border underlines the importance of the current invention.

To prevent its further spread, early diagnosis before the appearance of the dreaded symptoms is particularly important. However, the unculturable nature of the bacteria and their low concentration and uneven distribution in the hosts make it extremely difficult to detect *Ca. L.* infection. Instead of focusing on the bacteria, the disclosure provides a method of early diagnosis by taking advantage of host rapid defense responses to identify unique host biomarkers.

Some host small RNAs are rapidly and specifically induced by pathogens, which makes them one of the most attractive markers for early diagnosis. To identify HLB specific small RNAs, endogenous small RNAs were profiled by high-throughput sequencing of small RNA libraries prepared from HLB positive and uninfected control plants. Those small RNAs that are induced by HLB infection have the potential to serve as early detection diagnosis markers for HLB.

The disclosure also provides the identification of a major cause for the pathogenesis of HLB—phosphorus starvation—from the study of one HLB-induced miRNA, microRNA399 (miRNA399), which is one of the potential early diagnosis markers. miRNA399 is induced specifically in response to *Ca. Liberibacter* infection, but not to other bacterial pathogen, such as *Spiroplasma citri*, the causal agent for citrus stubborn disease that has similar symptoms. miRNA399 induction is an important response to phosphorous starvation. The level of phosphorus in *Ca. L.*-infected plants was only 60-70% of that in uninfected plants. Phosphorus application can largely rescue the symptoms and increase the yield of fruits.

Accordingly, the disclosure provides methods and compositions for treating *Ca. L.* infection comprising contacting the plant with a phosphorus oxyanion solution. The disclosure also provides methods for treating *Ca. L.* infection comprising down-regulating expression of the ubiquitin-conjugating enzyme (UBC) gene, which subsequently derepresses phosphorus transporters and increases phosphorus uptake.

By profiling small RNAs from untreated and Ca. *Liberibacter*-infected *Citrus sinensis* (sweet orange) samples using high throughput deep sequencing, some Huanglongbing-induced small interfering RNAs (siRNAs) and microRNAs (miRNAs) were identified, providing a method of early diagnosis for infection. Furthermore, one of these markers, miR399, is induced by phosphorus starvation. It targets ubiquitin E2 conjugating enzyme genes involved in phosphorus uptake, which has been demonstrated in *Arabidopsis thaliana*. This result indicates that phosphorus starvation is one of the causes for HLB disease symptom. Indeed, a markedly decreased level of phosphorus in *Ca. Liberibacter* infected citrus was observed. *Ca. Liberibacter* infection causes phosphorus starvation, and subsequently leads to quick induction of miR399, which in turn silences UBC and derepresses the phosphorus transporters and facilitates phosphorus accumulation. Thus, the disclosure also provides a method of treating HLB by applying phosphorus oxyanion solutions (including phosphite and phosphate salt solutions with polymeric forms) to *Ca. Liberibacter*-infected plants to reduce HLB symptoms.

The disclosure provides a method of determining infection of a plant or tree (e.g., a citrus plant or tree) comprising determining the level of miR399, siR1005, siR1008, and siR1009 in a sample from the plant or tree, wherein an increased level compared to an uninfected or healthy plant indicates that the plant or tree may be infected by *Ca. Liberibacter*.

The disclosure also provides a method of slowing or inhibiting the spread, growth or infection of a tree or plant with Ca. *Liberibacter* comprising contacting a plant with HLB disease or infected with *Ca. L.* with phosphorus oxyanions (which can be in solution), stimulating phosphorus uptake in the plant by suppressing expression of UBC mRNA or UBC polypeptide in the plant, thereby ameliorating symptoms of HLB disease in the plant.

Detection of Infection or Disease

The present methods detect the expression of small RNAs in citrus plants that are induced by infection with bacterial pathogens. In one embodiment, the bacterial pathogen is *Ca. Liberibacter*. In one embodiment, the bacterial pathogen is *Ca. Liberibacter asiaticus* (Las).

In some embodiments, infection of a citrus plant by *Ca. L.* induces or increases the expression level of some small RNAs. In some embodiments, infection of a citrus plant by *Ca. L.* induces or increases the expression of miRNA399, siRNA1005, siRNA1008 and/or siRNA1009 compared to a control or healthy plant.

In some embodiments, the small RNA molecules include the sequences shown in Table 1.

TABLE 1

Sequences of small RNA molecules that are increased following infection with *Ca. L.*

| small RNA | Sequence | SEQ ID NO: |
|---|---|---|
| csi-miR399a: | UGCCAAAGGAGAUUUGCCCGG | 9 |
| csi-miR399b: | UGCCAAAGGAGAGUUGCCCUA | 10 |
| csi-miR399c: | UGCCAAAGGAGAAUUGCCCUG | 11 |
| csi-miR399d: | UGCCAAAGGAGAGUUGCCCUG | 12 |
| csi-miR399e: | UGCCAAAGGAGAAUUGCCCUG | 11 |
| csi-siR1005: | ATAGATAATGGATCAACGGTTATA | 13 |
| csi-siR1008: | TCGAACAAGGTAAGGATGTCA | 14 |
| csi-siR1009: | CTTCTAATAAACATGCATGAA | 15 |

As is well known in the art, in RNA uracil (U) replaces thymide (T). Thus, T can be represented by T or U, depending if the sequence is DNA or RNA.

As is understood in the art, the sequence of siRNAs can vary at the 5' and 3' ends. Thus, for the detection of siR1008 and siR1009, the sequence detected can be shifted either 5' or 3' relative to SEQ ID NOs: 14 and 15. Thus, for siR1008, the detected sequence can include a sequence from CCTTGTTCGAACAAGGTAAGGATGTCATTCTTT (SEQ ID NO:100), where SEQ ID NO:14 is underlined. Likewise, for siR1009, the detected sequence can include a sequence from CGTCTTCTAATAAACATGCATGAACTTATT (SEQ ID NO:101), where SEQ ID NO:15 is underlined.

In some embodiments, infection of a citrus plant by *Ca. L.* reduces or decreases the expression level of some small RNAs. In some embodiments, infection of a citrus plant by *Ca. L.* reduces or decreases the expression level of a small RNA selected from miR408, miR171, miR396, miR398, miR160, and/or miR394 compared to a control or healthy plant.

FIG. 1 shows miRNAs that have increased expression levels in citrus plants infected with Las. Thus, in some embodiments, infection of a citrus plant by *Ca. L.* induces or increases the expression level of a micro RNA of Table 2.

TABLE 2

| miRNAs showing a relative increase in expression in citrus plants infected by Ca. L. |
|---|
| miR399 |
| miR159 |
| miR393 |

FIG. 1 also shows that infection of a citrus plant by *Ca. L.* reduces or decreases the expression level of other micro RNAs. Thus, in some embodiments, infection of a citrus plant by *Ca. L.* reduces or decreases the expression level of a microRNA shown in Table 3. In some embodiments, infection of a citrus plant by *Ca. L.* reduces or decreases the expression level of a small RNA selected from miR408, miR171, miR396, miR398, miR160, and/or miR394.

TABLE 3

| miRNAs showing relative decrease in expression in citrus plants infected by Ca. L. |
|---|
| miR160 |
| miR164 |
| miR398 |
| miR394 |
| miR403 |
| miR396 |
| miR171 |
| miR408 |
| miR172 |

As is well understood in the art, miRNA molecules are thought to degrade target mRNA or inhibit translation of RNA by precise or imprecise base-pairing with their target RNA molecules. Thus, the sequences of miRNA molecules can vary slightly from their target sequence and still function to inhibit gene expression. Further, the sequences of miRNA and siRNA molecules can vary at either the 5' or 3' end by the addition or subtraction of one or two nucleotides and still function to inhibit expression of a given target. Thus, the methods encompass detecting miRNA and siRNA molecules that have slight variations in the nucleic acid sequence.

For example, as shown in Table 4, different sequences were identified for miRNA399 in both uninfected control and *Ca. L.* infected citrus plants. The miR399 sequences shown in Table 4 are capable of targeting (base-pairing with) the mRNA that encodes the citrus UBC protein (accession number EY742134) or an mRNA substantially identical to the mRNA that encodes accession number EY742134. In one embodiment, the miR399 sequence targets a sequence that is substantially identical to SEQ ID NO:84.

TABLE 4

Citrus miRNA399 sequences and abundance upon *Ca. L. asiaticus* infection.

| | SEQ ID NO: | Reads | Alignment subject | Citrus small RNA sequence (reverse-complemented if orientation is -) |
|---|---|---|---|---|
| Untreated 10 wpi | 2 | 2 | ath-miR399b | TGCCAAAGGAGAGTTGCCCTA |
| | 1 | 1 | ath-miR399b | TGCCAAAGGAGAGTTGCCCTG |
| HLB 10 wpi | 1 | 12 | ath-miR399b | TGCCAAAGGAGAGTTGCCCTG |
| | 2 | 10 | ath-miR399b | TGCCAAAGGAGAGTTGCCCTA |
| | 3 | 1 | ath-miR399c | TGCCAAAGGAGCGTTGCCCTG |
| | 4 | 1 | ath-miR199b | TGCCAAAGGAGAGTTGCCATG |
| | 5 | 1 | ath-miR399c | TGTCAAAGGAGAGTTGCCCTG |
| Untreated 14 wpi | 2 | 2 | ath-miR399b | TGCCAAAGGAGAGTTGCCCTA |
| | 8 | 2 | ath-miR399f | TGCCAAAGGAGATTTGCCCGG |
| | 6 | 1 | ath-miR399a | TGCCAAAGGAGAATTGCCCTG |
| HLB 14 wpi | 2 | 23 | ath-miR399b | TGCCAAAGGAGAGTTGCCCTA |
| | 1 | 8 | ath-miR399b | TGCCAAAGGAGAGTTGCCCTG |
| | 7 | 1 | ath-miR399c | TGCTAAAGGAGAGTTGCCCTA |
| | 99 | | consensus miR399 | TG C/T C/T AAAGGAG A/C G/T/A TTGCC C/A T/G A/G |

Thus, in some embodiments, the method comprises detecting the expression level of a sequence that is substantially identical to one of the miR399 sequences in Table 4. For example, in some embodiments, a sequence that is at least 60%, 70%, 80%, 85%, 90%, or 95% identical to a sequence in Table 4 is detected. In one embodiment, the method comprises detecting a small RNA having the miR399 consensus sequence TG $X_1$ $X_2$ AAAGGAG $X_3$ $X_4$ TTGCC $X_5$ $X_6$ $X_2$ (SEQ ID NO:99), where $X_1$ is C or T, $X_2$ is C or T, $X_3$ is A or C, $X_4$ is G, T, or A, $X_5$ is C or A, $X_6$ is T or G, and $X_2$ is A or G.

In some embodiments, infection of a citrus plant by *Ca. L.* can be detected by detecting the expression level of a sequence that is substantially identical to an siRNA listed in Table 5. For example, in one embodiment, the expression level of a sequence that is at least 80%, 85%, 90%, or 95% identical to an siRNA listed in Table 5 is detected.

TABLE 5

HLB induced citrus siRNAs.

| reads with highest copy number (SEQ ID NO:) | untreated 10 wpi | HLB 10 wpi | H/U 10 wpi | untreated 14 wpi | HLB 14 wpi | H/U 14 wpi | Total |
|---|---|---|---|---|---|---|---|
| TTCCAGATAGAAGGCCACTCA (42) | 1.0 | 736.0 | 736.0 | 1.0 | 106.0 | 106.0 | 844 |
| TTCCACCAATCGATCAGGATA (43) | 1.0 | 233.0 | 233.0 | 1.0 | 89.0 | 89.0 | 324 |
| GCGTATGAGGAGCCATGCATA (44) | 1.0 | 155.0 | 155.0 | 1.0 | 115.0 | 115.0 | 272 |
| CTTGGATTTATGAAAGACGAA (45) | 1.0 | 127.0 | 127.0 | 1.0 | 1.0 | 1.0 | 130 |
| GGCAGGGCTAGTGACTGGAGTGA (46) | 1.0 | 117.0 | 117.0 | 1.0 | 37.0 | 37.0 | 156 |
| ACAGGCCGCAAACATTTTCCT (47) | 1.0 | 87.0 | 87.0 | 42.0 | 143.0 | 3.4 | 273 |
| ACAGACCGCACACCTTTTCTT (48) | 1.0 | 59.0 | 59.0 | 18.0 | 62.0 | 3.4 | 140 |
| ATTAGGAGCTAAAATTGTTGT (49) | 1.0 | 45.0 | 45.0 | 24.0 | 111.0 | 4.6 | 181 |
| ACGAAATGTGAGTAGAGTGGACAG (50) | 1.0 | 45.0 | 45.0 | 113.0 | 135.0 | 1.2 | 294 |
| TTCCAAAGGGATCGCATTGA (51) | 1.0 | 42.0 | 42.0 | 1.0 | 77.0 | 77.0 | 121 |
| TCATTTAAGGGTTTCGTGTTC (52) | 1.0 | 34.0 | 34.0 | 1.0 | 115.0 | 115.0 | 151 |
| ACGCTCGGACGAAGCACATAGATG (53) | 1.0 | 29.0 | 29.0 | 58.0 | 40.0 | 0.7 | 128 |
| TATGGGATTTACCTCGGCAAA (54) | 2.0 | 55.0 | 27.5 | 1.0 | 48.0 | 48.0 | 106 |
| TGTGTGGATGAATAAGATTTC (55) | 8.0 | 210.0 | 26.3 | 7.0 | 193.0 | 27.6 | 418 |

TABLE 5-continued

HLB induced citrus siRNAs.

| reads with highest copy number (SEQ ID NO:) | untreated 10 wpi | HLB 10 wpi | H/U 10 wpi | untreated 14 wpi | HLB 14 wpi | H/U 14 wpi | Total |
|---|---|---|---|---|---|---|---|
| TATCTGGATAAAAGGCTACCC (56) | 212.0 | 5229.0 | 24.7 | 211.0 | 3480.0 | 16.5 | 9132 |
| TCATGGATAAGGTCATGCATT (57) | 6.0 | 137.0 | 22.8 | 6.0 | 188.0 | 31.3 | 337 |
| AAAAACTTGGAAGCGTTGGAT (58) | 8.0 | 154.0 | 19.3 | 10.0 | 62.0 | 6.2 | 234 |
| TCCTGCCGGGTTGCATAATCA (59) | 6.0 | 85.0 | 14.2 | 1.0 | 19.0 | 19.0 | 111 |
| ATAGATAATGGATCAACGGTTATA (60) | 26.0 | 359.0 | 13.8 | 37.0 | 321.0 | 8.7 | 743 |
| TCATGGATAAGGTCATGCATC (61) | 25.0 | 308.0 | 12.3 | 24.0 | 403.0 | 16.8 | 760 |
| CTGAAAGCTGAGGTTGTCCTT (62) | 8.0 | 44.0 | 5.5 | 25.0 | 30.0 | 1.2 | 107 |
| AGTGTCAAAAAGAGCAATGGCGTC (63) | 11.0 | 44.0 | 4.0 | 25.0 | 22.0 | 0.9 | 102 |
| AATCCTTGGATTAGGAGTGTGGAG (64) | 1.0 | 4.0 | 4.0 | 1.0 | 112.0 | 112.0 | 118 |
| ATCAATAAATCAGGATTGGCGGAA (65) | 82.0 | 288.0 | 3.5 | 71.0 | 216.0 | 3.0 | 657 |
| CGTTAGGGAGTCCGGAGACGT (66) | 13.0 | 44.0 | 3.4 | 20.0 | 37.0 | 1.9 | 114 |
| GAATAAGACATGGAGTTGGAA (67) | 18.0 | 51.0 | 2.8 | 48.0 | 64.0 | 1.3 | 181 |
| AGGAAATGGACGATACGGACGCAT (68) | 70.0 | 176.0 | 2.5 | 91.0 | 1.0 | 0.0 | 338 |
| TCAAGTGAGGTTCGGTCTTTGAA (69) | 29.0 | 69.0 | 2.4 | 22.0 | 26.0 | 1.2 | 146 |
| TAATCGTGGGAGACGAAGCTG (70) | 2184.0 | 5128.0 | 2.3 | 2352.0 | 2587.0 | 1.1 | 12251 |
| CGAAGGTCCGAGGTCGAGGTT (71) | 68.0 | 154.0 | 2.3 | 82.0 | 1.0 | 0.0 | 305 |
| AGGTTTGGGCTTGTTGCAAGTAGA (72) | 27.0 | 61.0 | 2.3 | 45.0 | 25.0 | 0.6 | 158 |
| TCCGGGCGGAAGACATTGTCA (73) | 49.0 | 109.0 | 2.2 | 37.0 | 76.0 | 2.1 | 271 |
| AACGGAAAGAACACAACACGG (74) | 736.0 | 1592.0 | 2.2 | 924.0 | 673.0 | 0.7 | 3925 |
| TGTTAGCTTTCTCGGACGCAG (75) | 24.0 | 48.0 | 2.0 | 16.0 | 37.0 | 2.3 | 125 |
| TCAAGTGAGGTTCTGTCTTTGA (76) | 12.0 | 24.0 | 2.0 | 8.0 | 74.0 | 9.3 | 118 |
| AAAGCAACGATTGTATGGCCA (77) | 44.0 | 87.0 | 2.0 | 33.0 | 25.0 | 0.8 | 189 |
| TCAAGTGAGGTTCGGTCTTGA (78) | 146.0 | 260.0 | 1.8 | 116.0 | 253.0 | 2.2 | 775 |
| GAATGTGGAATTAAGCGCACCAAA (79) | 259.0 | 455.0 | 1.8 | 23.0 | 71.0 | 3.1 | 808 |
| TCGAACAAGGTAAGGATGTCA (80) | 197.0 | 301.0 | 1.5 | 180.0 | 577.0 | 3.2 | 1255 |
| CTGGATGCAACTGTGGTACGG (81) | 67.0 | 76.0 | 1.1 | 100.0 | 236.0 | 2.4 | 479 |
| GGTGCTTCCGGATCTCAGGAT (82) | 1.0 | 1.0 | 1.0 | 1.0 | 312.0 | 312.0 | 315 |
| CACATGGGTTAGTCGATC (83) | 1.0 | 1.0 | 1.0 | 1.0 | 750.0 | 750.0 | 753 |

H/U = ratio of reads from HLB diseased plants and uninfected plants.

In some embodiments, infection of a citrus plant by *Ca. L.* is determined by detecting the expression of one, two, three, four, five or more of the small RNAs from Tables 1, 2, 3, 4 or 5. In some embodiments, infection of a citrus plant by *Ca. L.* is determined by detecting the expression of one, two, three, four, five or more small RNAs that are substantially identical to a small RNA from Tables 1, 2, 3, 4 or 5.

Methods of detecting small RNAs are well known in the art and such methods can be adapted to detect miRNA399, siRNA1005, siRNA1008 and/or siRNA1009. In some embodiments, detection can include methods involving hybridization of nucleic acids to small RNAs by base-pairing. Examples include Northern analysis, polymerase chain reaction (PCR), reverse-transcription-PCR (RT-PCR) and microarrays. In some embodiments, the small RNA is detected by DNA oligonucleotides in Northern blot analysis. In some embodiments, the small RNA is detected using a locked nucleic acid (LNA) probe in Northern blot analysis.

In some embodiments, the amount of a small RNA detected is compared to the amount of small RNA detected in a control, uninfected plant to determine if the plant is infected by *Ca. L.* In some embodiments, the amount of a small RNA detected is compared to a reference value that corresponds to or is indicative of the level of expression of the particular small RNA in a plant that is not infected by *Ca. L.* In some embodiments, the expression of one, two, three, four, five or more small RNAs is detected.

In some embodiments, the small RNA is detected using a nucleic acid "dipstick" or other rapid detection device.

In some embodiments, the small RNA is detected by sequencing the isolated RNA. Thus, in some embodiments, the small RNA is cloned and sequenced to determine the nucleic acid sequence of the small RNA, thereby detecting the expression of the small RNA in a plant. In some embodiments, the expression of a small RNA is detected by determining the number of sequencing reads that correspond to the individual small RNA sequence. In one embodiment, the number of sequencing reads that correspond to an individual small RNA sequence is compared in infected and uninfected control plants, thereby providing an indication that the infection increased or decreased expression of the small RNA.

In some embodiments, the small RNAs were cloned and sequenced as described in the Examples. For example, total RNA is isolated from a plant tissue, 18-28 nucleotide fragments are recovered, and the purified fragments are ligated to adaptor oligonucleotides at the 5' and 3' ends. In one embodiment, the adaptor oligonucleotides serve as binding sites for PCR primers. The RNA fragments with the adaptor oligonucleotides are reverse transcribed and amplified by PCR. The PCR amplified products are sequenced to detect the small RNA molecules expressed by the plant.

The sequencing results revealed that the small RNAs induced by Las infection were from about 18 to about 28 nucleotides in length. In some embodiments, the small RNAs were identified as microRNAs (miRNAs) by aligning the sequence with conserved miRNAs in other plant species (less than or equal to 2 mismatches to a conserved miRNA). In some embodiments, the small RNAs were identified as miRNAs based on whether their precursor RNAs can form stem-loop structures. In some embodiments, the small RNA was identified as a putative small interfering RNA (siRNA) because it did not match any conserved plant miRNA or its precursor RNA did not form stem-loop structures.

In some embodiments, the small RNA comprises a 21, 22, 23, or 24 nucleotide species.

In some embodiments, increased expression is detected when the expression level of a small RNA is at least 10%, 20%, 50%, 100%, 500% or 1000% or more than the expression level detected in a control or uninfected plant. In some embodiments, decreased expression is detected when the expression level of a small RNA is less than 10%, 20%, 50%, 100%, 500% or 1000% or less than the expression level detected in a control or uninfected plant. In some embodiments, the control level corresponds to the expression level of a particular small RNA in a healthy plant that does not have HLB disease. In some embodiments, the control level is a reference value or average value that corresponds to or is indicative of the level of expression of the particular small RNA in a plant or population of plants that is not infected by *Ca. L.*

Samples

In some embodiments, the expression of a small RNA is detected in a biological sample from a citrus plant. For example, the biological sample can comprise bark or a leaf from an infected or control plant.

Methods of Treating

The present disclosure also provides methods of ameliorating the symptoms of HLB infection of citrus plants. The methods described herein can be used to reduce symptoms caused by HLB infection, including yellowing of leaves, blotchy mottle of the leaves, zinc-deficiency-like mottle, severe chlorosis, and reduced fruit yield. It will be understood that symptoms of HLB vary according to the time of infection, stage of the disease, tree species, and tree maturity, among other things. It will be further understood that the disclosed methods do not necessarily result in eradication or cure of the infection, but can significantly reduce the symptoms caused by HLB infection.

Thus, in some embodiments, the methods provided herein reduce the symptoms of HLB by reducing the yellowing of leaves, resulting in a greener appearance, increasing the growth rate of the plant, and/or increasing the fruit yield of the plant. Thus, in some embodiments, the fruit yield is improved by 5%, 10%, 20%, 30%, 40%, 50%, 60% 70%, 80%, 90%, 100%, 200%, 500% of more compared to a plant that is not treated according to the methods. In some embodiments, the fruit yield is increased to 10%, 20%, 30%, 40%, 50%, 60%, 70%, 80%, 90%, or 100% of the yield of a similar plant that was not infected by HLB.

In some embodiments, the methods involve contacting an infected plant with inorganic phosphite and/or phosphate (Pi). In one embodiment, the inorganic phosphite and/or phosphate is in a solution. In some embodiments, the plant is contacted with a phosphorus solution comprising phosphorus oxyanion solutions (including phosphate and phosphate salt solutions). In one embodiment, the phosphorus solution comprises mixed mono- and dipotassium salts of phosphorus acid, with polymeric forms. In one embodiment, the inorganic phosphorus solution is applied by foliar spray.

In some embodiments, the method of treatment can include transforming a plant with an expression cassette that expresses a small RNA described herein. For example, in one embodiment, a citrus plant can be transformed with an nucleic acid that expresses miR399. While not being bound by theory, it is believed that expression of miR399 regulates a conserved phosphate homeostasis pathway, which results in increased transport of Pi into the plant cells. Thus, in one embodiment, the method comprises overexpressing miR399 in a plant. In one embodiment, the method comprises stimulating phosphate fixation or accumulation in the plant.

In some embodiments, the method of treatment includes suppressing or decreasing the expression or activity of a ubiquitin conjugating enzyme (UBC), for example ubiquitin-conjugating enzyme E2. In one embodiment, the citrus ubiquitin conjugating enzyme has accession number EY740382. In one embodiment, the ubiquitin conjugating enzyme is a citrus homolog of the *Arabidopsis* PHO2 (phosphate 2) ubiquitin conjugating enzyme E2. In one embodiment, the citrus UBC is encoded by the sequence shown in SEQ ID NO:84.

In one embodiment, the method of treatment includes increasing the expression or activity of Pi transporters. For example, in some embodiments, the Pi transporters are citrus homologs of the *Arabidopsis thaliana* phosphate transporter 2 (AtPT2) and phosphate transporter 2;1 (AtPHT2:1). In some embodiments, the citrus phosphate transporter homologs are represented by Unigene Csi: 14938 (UGID: 3374895) and Unigene Csi: 9842 (UGID: 2916608).

Expression Cassettes

In some embodiments, the present invention provides for expression cassettes comprising a promoter operably linked to a polynucleotide encoding a small RNA of the invention (e.g., as described herein), wherein introduction of the expression cassette into a plant results in the plant expressing a small RNA as described herein. In some embodiments, the promoter is heterologous to the polynucleotide. In some embodiments, the promoter is inducible. In some embodiments, the promoter is tissue-specific.

In some embodiments, introduction of the expression cassette into a plant results in the plant having decreased expression or activity of a UBC as compared to a plant lacking the expression cassette. In one embodiment, the introduction of the expression cassette into a plant results in the plant having decreased expression or activity of the citrus homolog of ubiquitin conjugating enzyme E2. In some embodiments, introduction of the expression cassette into a plant results in the plant having increased expression or activity of Pi transporters as compared to a plant lacking the expression cassette. In one embodiment, introduction of the expression cassette into a plant results in the plant having increased expression or activity of the citrus homolog of phosphate transporter 2 (AtPT2) and phosphate transporter 2;1 (AtPHT2:1).

In another embodiment, the present invention provides for expression vectors comprising an expression cassette of the invention (e.g., as described herein).

Plants

In some embodiments, the plant is a citrus plant. In some embodiments, the citrus plant is an orange tree, a lemon tree, a lime tree, or a grapefruit tree. In one embodiment, the citrus plant is a navel orange, Valencia orange, sweet orange, mandarin orange, or sour orange. In one embodiment, the citrus plant is a lemon tree. In one embodiment, the citrus plant is a lime tree. In some embodiments, the plant is a relative of a citrus plant, such as orange jasmine, limeberry, and trifoliate orange.

In some embodiments, the present invention provides for plants (or a plant cell, seed, flower, leaf, fruit, or other plant part from such plants or processed food or food ingredient from such plants) comprising an expression cassette comprising a promoter operably linked to a polynucleotide encoding a small RNA of the invention (e.g., as described herein). In some embodiments, the plant has decreased UBC expression or activity and/or increased expression or activity of Pi transporters.

Kits

In some embodiments, the disclosure provides kits that are useful for detecting the expression of small RNAs in plants. For example, the kit can include reagents that detect the presence of one or more small RNAs in a sample from a plant. In some embodiments, each reagent detects a different small RNA. In some embodiments, the reagent comprises a ligand that is capable of specifically binding to or hybridizing with a small RNA described herein. In some embodiments, the reagent is a nucleic acid that is labeled with a probe or other moiety that enables detection of the reagent. In some embodiments, the reagents include the nucleotide sequences in Tables 1-5 above. In some embodiments, the reagents are capable of detecting one, two, three, four, five or more of the small RNAs described herein.

In some embodiments, the kits include primers that are useful for amplifying the small RNAs detected by the kits. For example, the kits can include the following primer sequences:

```
miR399b (SEQ ID NO: 2):
TGCCAAAGGAGAGTTGCCCTA miR399b RT primer (SEQ ID NO: 85):
GTCGTATCCAGTGCAGGGTCCGAGGTATTCGCACTGGATACGACATGGGC
(50 nt)

PCR primer:
miR399b RT-F (SEQ ID NO: 86):
GCGGCGGTGCCAAAGGAGAGTT miR399b RT-R (SEQ ID NO: 87):
GTGCAGGGTCCGAGGT csi-siR1005 (SEQ ID NO: 13):
ATAGATAATGGATCAACGGTTATA csi-siR1005 RT primer (SEQ ID NO: 88):
GTCGTATCCAGTGCAGGGTCCGAGGTATTCGCACTGGATACGACGTTATA
(50 nt)

PCR primer:
csi-siR1005 RT-F (SEQ ID NO: 89):
GCGGCGGATAGATAATGGATCAACG csi-siR1005 RT-R (SEQ ID NO: 90):
GTGCAGGGTCCGAGGT csi-siR1008 (SEQ ID NO: 14):
TCGAACAAGGTAAGGATGTCA csi-siR1008 RT primer (SEQ ID NO: 91):
GTCGTATCCAGTGCAGGGTCCGAGGTATTCGCACTGGATACGACATGTCA
(50 nt)

PCR primer:
csi-siR1008 RT-F (SEQ ID NO: 92):
GCGGCGGTCGAACAAGGTAAGG csi-siR1008 RT-R (SEQ ID NO: 93):
GTGCAGGGTCCGAGGT csi-siR1009 (SEQ ID NO: 15):
CTTCTAATAAACATGCATGAA csi-siR1009 RT primer (SEQ ID NO: 94):
GTCGTATCCAGTGCAGGGTCCGAGGTATTCGCACTGGATACGACCATGAA
(50 nt)

PCR primer:
csi-siR1009 RT-F (SEQ ID NO:95):
GCGGCGGCTTCTAATAAACATG csi-siR1009 RT-R (SEQ ID NO: 96):
GTGCAGGGTCCGAGGT.
```

EXAMPLES

Example 1

This example describes methods for detecting and treating citrus plants infected with *Ca. L. asiaticus* ("Las").

Materials and Methods

Plant Material Maintains, Inoculation, and RNA Extraction

For examining Las induced small RNA, two-year-old greenhouse-grown 'Navel' orange (*C. sinensis*) scions on Cleopatra mandarin (*C. reticulata*) rootstocks were inoculated by grafting a combination of tree bark pieces or leaf pieces onto the rootstock portion of each plant. Five plants were inoculated with bacterium-free tissue pieces and 19 plants were inoculated with infected tissue for 10 and 14 weeks post inoculation (wpi), respectively. For infected plants, bark and leaf pieces were obtained from infected greenhouse-grown Valencia scions. For non-infected plants, bark and leaf pieces were obtained from a healthy greenhouse-grown Valencia orange, confirmed negative for Las by PCR. For examining *Spiroplasma citri* induced small RNA, Spring Navel/Carrizo was grafted to Madam Vinous (*C. sinensis*) receptor plants, which are positive for *S. citri* by culturing and PCR using primers to spiralin gene sequences. Before inoculation plants were fertilized using a 17N-6P-10K controlled release fertilizer (Scotts Sierra, Marysville, Ohio, USA). Plants were arranged randomly on the greenhouse bench and kept under natural light conditions at a temperature of 17-25° C.

Small RNA Library Construction

Total RNA was resolved by a denaturing 14% polyacrylamide gel. 18-28 nt RNA fragments were recovered. The purified fragments were 5' adapted (GUU CAG AGU UCU ACA GUC CGA CGA UCA G; SEQ ID NO:97), gel purified, and 3' adapted (UC GUA UGC CGU CUU CUG CUU G; SEQ ID NO:98). The RNA fragments adapted at both ends were gel purified and reverse transcribed (SuperScript II, Invitrogen). After PCR amplification for 15 cycles (98° C. for 30 sec; 98° C. for 10 sec; 60° C. for 30 sec), the PCR products were gel purified and sequenced according to Solexa small RNA sequencing protocol.

Mineral Measurement

For mineral analysis, six to eight leaves were collected from each plant for analysis. Leaves from two non-infected plants of the same age and the same scion/rootstock combination were collected for comparison. Leaf tissue was washed for 15 sec each in RO-D (reverse osmosis-distilled) water, 0.01% detergent (Citranox, Alconox, Inc., White Plains, N.Y.) and 0.1 N HCl solution, followed by three more rinses in RO-D water, dried at 80° C. for at least 24 h in a forced-air oven, dry weight recorded, and leaf tissue milled to pass a 20-mesh screen. Leaf tissue (500 mg) was digested in 10 ml of concentrated HNO3 (trace metal grade) at 300 psi and 170° C. for 10 min in a microwave (model Mars 5, CEM Corp., Mathews, N.C.). Leaf digestates were brought to volume in 100 ml volumetric flasks and filtered (no. 41; Whatman Paper, Maidstone, Kent, U.K.). Foliar levels of phosphorous (P), potassium (K), iron (Fe), manganese (Mn), copper (Cu), zinc (Zn), sodium (Na), calcium (Ca), and magnesium (Mg) were determined by inductively couple plasma (ICP [IRIS 1000 HR Duo, ThermoElemental, Franklin, Mass.]) and nitrogen (N) and carbon (C) by dynamic-flash combustion and GC separation (CNS analyzer [NC 2100, CE Elantech, Inc., Lakewood, N.J.]).

Application of Inorganic Phosphorus Solution

The foliar nutrient sprays started with the spring flush in 2008. Applications have been made three times each year and timed with the initiation of the new vegetative flushes in the spring (March), summer (June), and autumn, (September). The foliar spray treatment has been a 3-18-20 analysis liquid fertilizer of potassium poly phosphate with 1.0 pint/gal. mono- and dipotassium salts of phosphorus acid 56% (K-Phite, Plant Food Systems, Inc., Zellwood, Fla. 32798), plus 8.4 lbs. spray grade potassium nitrate ($KNO_3$), and 5.0 gallons 435 citrus spray oil in 250 gal./acre rate applied by hand gun to the foliage until runoff. Untreated control trees received no foliar applied nutrients. All trees received two ground-applied applications of a controlled-release fertilizer to the soil each year of a 14-0-24 analysis. The nutrients are from sulfur coated urea, sulfur coated sulfate of potash, ammonium nitrate, sulphate of potash magnesia, and muriate of potash. The fertilizer contained 2.3% Mg, 005% B, and 7.57% S. Insect management was determined by scouting and appropriate insecticides were applied by tractor pulled speed sprayer when required. Copper was used as a fungicide for disease control. Irrigation was by micro sprayers under each tree. Systemic and pre-emerge herbicides were used for weed management. Other standard good grove management practices known to favor good production were used.

PCR Detection of Las

The presence of Las was tested monthly and symptom-development was recorded. Petioles were ground in liquid nitrogen with a mortar and pestle. One hundred mg of ground tissue was used for DNA extraction according to the manufacturer's instructions (Qiagen, Valencia, Calif., USA). PCR amplifications were performed as described by Albrecht and Bowman (2008).

RNA Extraction

Total RNA was extracted from fully expanded leaves according to Strommer et al. (1993) with slight modifications. Phenol/chloroform/isoamylalcohol (25:24:1) extraction was followed by one extraction with chloroform/isoamylalcohol and precipitation of RNA with isopropanol at −20° C. overnight. RNA was pelleted by centrifugation at 10,000 g and 4° C. for 1 h. RNA pellets were stored at −80° C. and shipped to UC Riverside for construction of small RNA libraries. Leaf petioles were used for PCR detection of the bacterium.

Small RNA Parsing

After Illumina sequencing, the generated sequences (in FASTA format) were parsed and trimmed in total. An R program was used to identify the small RNA/adaptor boundaries, trim off the adaptors with variant length, and sort the sequences to respective source libraries. After removing the sequences shorter than 18 nt or longer than 28 nt, the remaining unique small RNAs were filtered by BLAST against a citrus non-coding RNA database, which included rRNA, tRNA, snoRNA and snRNA. The citrus non-coding RNA database was generated by combining Rfam database (Release 9.1, http://www.sanger.ac.uk/Software/Rfam/) with NCBI citrus EST sequences (http://www.ncbi.nlm.nih.gov/). The resulted small RNA sequences were interpreted as citrus small RNA and were studied in this research.

Small RNA Cluster Analysis and Annotation

Citrus EST sequences from NCBI (http://www.ncbi.nlm.nih.gov/) and non-redundant short EST sequences (<150 bps in length) parsed from the trace files (provided by Dr. Tim Close; UC Riverside) were assembled using CAP3 to generate a citrus EST Uniset database. The parsed small RNA sequences were then aligned to citrus EST Uniset database with BOWTIE (version 0.10.0, http://bowtie-bio.sourceforge.net/index.shtml), allowing up to 2 mismatches. Such generated sequences were mapped, and the reads for each source library was counted. To compare the expression level between different libraries, small RNA counts were normalized to the original library size. Cluster analysis on small RNAs matching to citrus EST Uniset was done by R program. A small RNA cluster was defined by aligning to the same locus with at least 16 nt overlapping. The clusters featured with forward (F) and reverse/complementary (R/C) alignments were counted in the 4 libraries, respectively. The functional annotation for citrus EST Uniset genes was from NCBI non-redundant protein database, *Arabidopsis* protein database (TAIR8_pep_20080412) and rice protein database (Version 5.0). Only the Uniset genes aligned with more than 10 small RNA copies were listed in the final small RNA expression table.

Conserved and Novel miRNA Analysis

For identifying conserved microRNAs, candidate small RNAs were analyzed by BLAST against microRNA Registry and Plant MicroRNA database (PMRD; http://bioinformatics.cau.edu.cn/PMRD/), respectively. For predicting novel miRNAs, each EST sequences matched with small RNAs were passed through an R script that detects a 450 bp pile-up matching region, and retrieve the flanking sequences by 200 bp from each side of the region. All retrieved EST fragments were folded with RNAfold (version 1.6.1). Structures of the EST sequences with minimum free energies were further analyzed by using an R and Perl script to retrieve stem-loops from the second structures and to check whether these stem-loops satisfy the following criteria: (1) the length of stem is longer than 20 bp; (2) no more than 4 bugles in a stem; (3) no more than 3 bp mismatches in a bugle; (4) putative microRNA locates on one strand of the stem, while miRNA* on the complementary strand; (5) no small RNA read matches to the loop region. Such predicted miRNAs were subjected to northern blot validation.

Conserved and Novel Citrus MicroRNA Target Prediction

MicroRNA targets were computationally predicted from the citrus EST Uniset using TargetFinder program (Release 1.5, http://jcclab.science.oregonstate.edu/node/view/56334) with default parameter settings. Briefly, potential targets from FASTA searches (+15/−10 match/mismatch scoring ratio, −16 gap penalty, and a RNA scoring matrix) were scored using a position-dependent, mispair penalty system. Penalties were assessed for mismatches, bulges, and gaps (+1 per position) and G:U pairs (+0.5 per position). Penalties were doubled if the mismatch, bulge, gap, or G:U pair occurred at positions 2 to 13 relative to the 5' end of the microRNA. Only one single-nt bulge or single-nt gap was allowed. Based on a reference set of validated microRNA targets, only predicted targets with scores of four or less were considered reasonable. The functional annotation for targets of conserved and novel microRNA was done from NCBI non-redundant protein database.

Northern Hybridization

Fifteen to 100 micrograms of total RNA were loaded per lane, depending on signal strength. The RNAs were resolved on a denaturing 14% polyacrylamide gel and electro-blotted onto Hybond N+ membranes (Amersham) overnight in a cold room at a constant 150 milliampere (Bio-Rad). Membranes were cross-linked with 0.15M 1-ethyl-3-[3-dimethylaminopropyl]carbodiimide hydrochloride (EDC) at 60° C. for 2 hours and dried at 80° C. for 2 hours. Citrus miRNA probes were synthesized as their reverse complementary sequences to the mature miRNAs and were labeled at the 5' end with $\gamma$-$^{32}$P-ATP using T4 polynucleotide kinase (Bio-labs). Membranes were pre-hybridized using Perfect Hyb Plus buffer (Sigma) for 2 hours and hybridized with probes overnight at 37° C. Membranes were exposed overnight either to storage phosphor screens (GE health) or X-ray films after being washed four times (20 min each).

Results

Small RNA Profiling of HLB-Positive and Healthy Sweet Orange

To study citrus small RNAs in responding to Las infection, *C. sinensis* plants were infected by Las by graft. Samples were collected at an early time point (10 wpi) and a late time point (14 wpi), respectively. Small RNAs ranging from 18 to 28 nucleotides (nt) from both healthy and Las-infected (treated) plants were cloned and sequenced. About half of the sequences can be aligned to the currently available citrus genome that was assembled from different databases. The identified citrus small RNAs were grouped into miRNAs and siRNAs by whether the sequence can be matched to conserved miRNAs (=<2 mismatches) in other plant species (top 20 plant species in miRBase; Table 6), and/or whether their precursor RNAs can form stem-loop structures. Our data showed that about 30% of the deep-sequencing reads belong to miRNA, while another 70% belong to siRNA due to the lack of miRNA characteristics. Since these citrus siRNAs didn't show any sequence similarities to siRNAs identified in other plant species or other organisms, we interpret them as *C. sinensis* specific siRNAs and named them as csi-siRNAs. Our deep-sequencing results showed that, similar to the model plant such as *Arabidopsis*, citrus small RNAs are featured by 21 nt and 24 nt species, as well as relatively low-abundant 22 and 23-nt populations. The majority of the identified citrus miRNAs start with a uracil (U), while most of the siRNAs start with both U and A (adenine).

TABLE 6 conserved citrus miRNAs and abundance in libraries.

| miRNA families | 10 wpi | | 14 wpi | | Total |
|---|---|---|---|---|---|
| | Untreated | HLB | Untreated | HLB | |
| miR157 | 31896 | 34020 | 46477 | 58511 | 170904 |
| miR166 | 2260 | 2345 | 69580 | 58393 | 132578 |
| miR167 | 8546 | 1916 | 2621 | 7820 | 20903 |
| miR164 | 4409 | 1775 | 2271 | 1227 | 9682 |
| miR172 | 2696 | 1440 | 2366 | 1199 | 7701 |
| miR165 | 123 | 108 | 4620 | 2790 | 7641 |
| miR168 | 1160 | 1827 | 1393 | 2324 | 6704 |
| miR159 | 109 | 749 | 321 | 1326 | 2505 |
| miR396 | 707 | 113 | 1173 | 139 | 2132 |
| miR845 | 855 | 234 | 311 | 209 | 1609 |
| miR169 | 220 | 84 | 343 | 424 | 1071 |
| miR403 | 612 | 104 | 104 | 42 | 862 |
| miR827 | 223 | 124 | 189 | 156 | 692 |
| miR160 | 159 | 66 | 406 | 41 | 672 |
| miR156 | 86 | 43 | 236 | 283 | 648 |
| miR170 | 215 | 129 | 97 | 195 | 636 |
| miR162 | 60 | 49 | 161 | 147 | 417 |
| miR393 | 16 | 66 | 22 | 271 | 375 |
| miR171 | 191 | 22 | 39 | 15 | 267 |
| miR394 | 23 | 8 | 101 | 19 | 151 |
| miR399 | 4 | 26 | 6 | 33 | 69 |
| miR398 | 10 | 4 | 23 | 5 | 42 |
| miR408 | 14 | 1 | 7 | 3 | 25 |
| miR390 | 7 | 4 | 3 | 4 | 18 |
| miR395 | 2 | 6 | 0 | 5 | 13 |
| miR397 | 3 | 0 | 3 | 4 | 10 |

Citrus miRNAs were searched against database containing miRNA sequences from *Arabidopsis thaliana, Brassica rapa, Populus trichocarpa* (western balsam poplar), *Gossy-* pium hirsutum (upland cotton), Brassica napus, Glycine max, Vitis vinifera (wine grape), Solanum lycopersicum, Medicago truncatula, Oryza sativa, Zea mays (maize), Triticum aestivum (bread wheat), Sorghum bicolor, Saccharum officinarum (noble cane), Hordeum vulgare subsp. vulgare, Pinus taeda, Ricinus communis, Selaginella moellendorffii, Physcomitrella patens, and Chlamydomonas reinhardtii. miRNAs with more than 10 reads were deemed as valid conserved miRNAs and reported in Table 6.

Research has shown that some Arabidopsis siRNAs that are specifically elicited upon bacterial pathogen infection participate in host innate immunity by regulating the expression level of their targets (Katiyar-Agarwal et al., 2006; Katiyar-Agarwal et al., 2007; Zhang et al., 2011). We investigated whether csi-siRNAs expression is altered upon Las-infection. We compared csi-siRNAs expression levels in both healthy and Las-infected samples and found that, similar in Arabidopsis, some csi-siRNAs also showed varied expression levels by Las infection (Table 5). Csi-siRNAs identified in this research were sorted according to their expression levels between healthy and treated samples and 10 representatives (csi-siR1001-10) were selected for experimental validation. Csi-siR1005 was induced upon Las infection both at 10- and 14-wpi. Csi-siR1005 can target a citrus protein without known function. Similarly, csi-siR1008 and csi-siR1009 also showed weak but noticeable induction upon Las infection. Csi-siR1008 can target a citrus protein homolog to an Arabidopsis putative disease resistance protein (CC-NBS class) with perfect match, whereas csi-siR1009 targets a putative disease resistance protein with 2 mis-matches. It suggests that csi-siR1008 and csi-siR1009 may play potential roles in citrus innate immunity by regulating the expression of disease resistance proteins. These inductions are specific to Las infection since when samples were treated with S. citri that causes citrus stubborn disease, no significant induction was observed.

We focused our study on citrus miRNAs, which have been more extensively studied compared to siRNAs. A potential advantage of focusing on miRNAs is that currently available information in other systems may facilitate the study in citrus. Our analysis showed that most of the citrus miRNAs (conserved plus novel miRNAs) are 21-nt long, and dominantly favored a U at the 5' end. Among the citrus miRNAs identified, about 240 miRNAs belonging to at least 26 miRNA families (reads>=10) could also be found in other plant species including Arabidopsis thaliana (Table 6), indicating that regulatory mechanisms in other plant species may also apply to the citrus system. Beyond these conserved miRNAs, 13 identified citrus miRNAs could not be matched to any currently known plant miRNAs, and therefore were termed as novel miRNAs. Similarly, they were named as csi-miRNAs (Table 7).

TABLE 7

Novel citrus miRNAs.

| Candidate ID | microRNA sequence (SEQ ID NO:) | microRNA star (SEQ ID NO:) | untreated 10 wpi | HLB 10 wpi | untreated 14 wpi | HLB 14 wpi |
|---|---|---|---|---|---|---|
| Csi-miR5001 | UGAAGCUGCCAGC AUGAUCU (16) | AUCAUCUGGCAGU UUCACC (17) | 7713.00 | 9946.31 | 625.47 | 776.91 |
| Csi-miR5002 | UAGAUAAAGAUGA GAGAAAAA (18) | UUUUCUCUUAUCG UUAUCUGU (19) | 604.00 | 104.13 | 675.33 | 235.24 |
| Csi-miR5003 | UUUGUUGCAUGAU GCUGAUAA (20) | CUACCCGCAUCAU GCAACAAA (21) | 99.00 | 212.42 | 227.75 | 53.65 |
| Csi-miR5004 | AGUGUUAGGUGUA GAGAAGCACGA (22) | UCUCGUACUUCUC UUCACCAAGCA (23) | 125.00 | 122.87 | 132.57 | 99.05 |
| Csi-miR5005 | AUUCGGGACGAGU UUACAAC (24) | CGUAAACUCGUCU CGUACUU (25) | 83.00 | 97.88 | 100.85 | 50.56 |
| Csi-miR5006 | AAUGGCUGGAUCC AGCUGUGG (26) | ACAAUUGGAUUUA GCCAUUAA (27) | 51.00 | 42.69 | 48.72 | 25.79 |
| Csi-miR5007 | AUGCCGUAUCACG UGGGAG (28) | CCCACUUGAUGUG UCAUUC (29) | 44.00 | 49.98 | 35.13 | 27.86 |
| Csi-miR5008 | UUUGAUGCCUUCU UUAGUCGC (30) | GAUUAAGGAGAGU UUUCAGU (31) | 5.00 | 10.41 | 18.13 | 10.32 |
| Csi-miR5009 | GACAGAAGAGAGT GAGCAC (32) | GCUCGCUCCUCUUC UGUCAG (33) | 0.00 | 5.21 | 0.00 | 31.98 |
| Csi-miR5010 | GUAUAUAUCUUGC AUGCAUG (34) | GUAUGUAAGAUAC AUCCCC (35) | 12.00 | 9.37 | 5.67 | 2.06 |
| Csi-miR5011 | UUUCUCUUAUCGU UAUCUGU (36) | UAGAUAAAGAUGA GAGAAAAA (37) | 17.00 | 1.04 | 3.40 | 3.10 |
| Csi-miR5012 | UUGUUGUUGAGUG UGUAUGUUA (38) | ACAUAAAUACUUA AUAAUAAUC (39) | 8.00 | 8.33 | 2.27 | 2.06 |
| Csi-miR5013 | UCGUCCUUCUCUC AUAUUUUU (40) | AGAGUGGGUGGGU GGAGAGG (41) | 1.00 | 4.17 | 6.80 | 1.03 |

*Reads are normalized to library sizes. Csi = citrus sinensis. wpi = weeks post infection.

The computationally predicted novel csi-miRNAs were experimentally validated using radioactively labeled probes. The Northern hybridization results showed a faithful agreement with the deep-sequencing results. For example, csi-miRNA5001, 5002, 5003, 5004, 5005, 5006, and 5007, which showed moderate or high reads in our deep-sequencing analysis, could be easily detected by their corresponding probes in Northern blots. In contrast, other csi-miRNAs that were predicted as low abundant appeared to be too weak to be detected (data not shown). This was confirmed by increasing the detecting limit by employing a locked nucleic acid (LNA) probe: when probed by a LNA probe, csi-miRNA5009 was clearly detected. However, there is no noticeable variation between healthy and treated samples, or between 10 wpi and 14 wpi time points, indicating that under the examined conditions, these csi-miRNAs may not be subject to expression alteration.

Some Citrus miRNAs and siRNAs are Differentially Expressed in Healthy and HLB-Positive Plants Computational analysis of our data revealed that some of the conserved citrus miRNAs showed elevated expression upon Las infection, while others showed reduced expression. For example, at 10 and 14 wpi, miRNAs such as miR159, 399, 393 are noticeably induced (>2 fold), while miRNAs such as miR160, 396, 394, 398, 171, 403, and 408 are clearly reduced (>2 fold), as shown in FIGS. 1a and 1b. This implies that these csi-miRNAs may be subject to the influence of Las infection, or even play some potential roles in Las-elicited plant immunity. We tested some of the miRNAs by using Northern hybridization. Our results showed that all these alterations in miRNA expression upon Las infection were successfully validated using sequence-specific probes against the family member with the highest reads (data not shown). This induction is specifically due to Las infection since S. citri infection didn't show noticeable alteration on miR399 and miR159 expression level.

Induction of miR399 Revealed Phosphorus Deficiency in HLB-Positive Plants

In spite of its relatively low abundance, miR399 showed distinguishable induction upon Las challenge (FIG. 1). MiR399 has been shown to be involved in phosphate (Pi) homeostasis in *Arabidopsis* (Fujii et al., 2005; Lin et al., 2008; Hsieh et al., 2009). Some studies have shown that miR399 is the phloem-mobile long-distance signal involved in phosphate starvation response (Buhtz et al., 2008; Pant et al., 2008; Buhtz et al., 2010). In *Arabidopsis thaliana*, miR399 has multiple target sites in the 5'UTR of the transcript of a gene encoding a putative ubiquitin-conjugating enzyme (PHO2; At2g33770), which in turn negatively regulates Pi transporters (PT) (Fujii et al., 2005; Bari et al., 2006; Lin et al., 2008). Upon Pi deficiency, the miR399-mediated Pi homeostasis mechanism was turned on: the Pi-deficiency-induced miR399 down-regulates PHO2, which releases its inhibitory role on PTs; the increased PTs transport more Pi into the cells as a consequence, which alleviates Pi deficiency (Fujii et al., 2005; Lin et al., 2008). Research showed that the same Pi regulatory mechanism might also exist in other plant species such as rapeseed (Buhtz et al., 2008) and pumpkin (Pant et al., 2008). Interestingly, Bari et al. (2006) identified potential orthologs of PHO2 from orange (*Citrus aurantium*), implying that the regulatory mechanism maybe also conserved in citrus plants.

The variation on citrus miR399 level between healthy and Las-treated citrus samples, and the potential conservation of the Pi regulatory mechanism prompted us to investigate the Pi level in these samples. We hypothesize that if the same Pi-regulatory mechanism also applies in *C. sinensis*, then the Las-infected *C. sinensis* would show deficiency in Pi level and elevated miR399 expression level; and we would also observe reduced PHO2 (citrus homolog) mRNA and increase PTs.

We collected leaves from both healthy and Las-infected plants (PCR-confirmed). Our measurement showed that the phosphorus level in leaves of treated plants was more than 35% lower than in leaves from untreated plants. We also observed iron (Fe) deficiency in Las-infected plants, which indicates the phloem localized bacterial pathogen confers similar negative influence on several mineral elements. However, homeostasis of entire mineral elements is not negatively affected since some elements showed no noticeable variation, such as potassium (K) and zinc (Zn) (FIG. 4a). In contrast, copper (Cu) accumulated more in Las-infected plants (data not shown).

Figure 4:
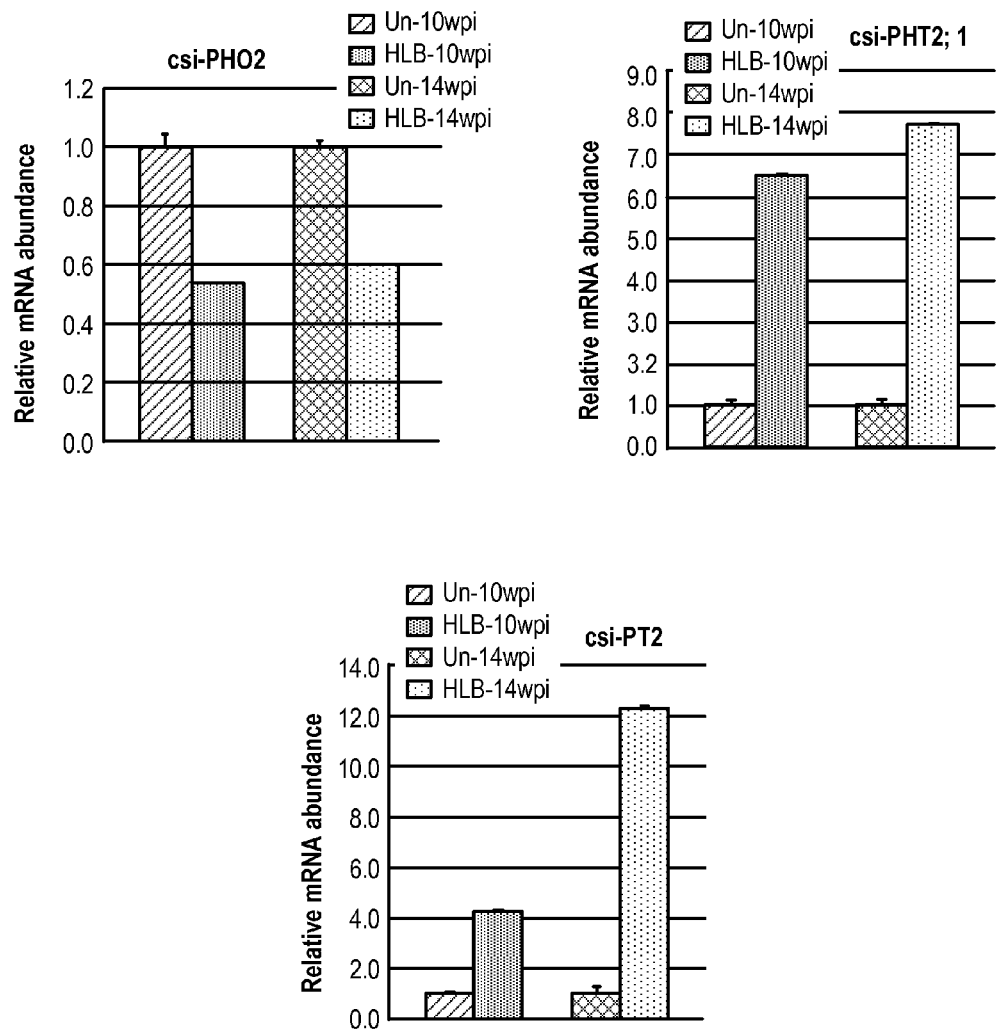
FIG. 4 shows Las infection down-regulates csi-PHO2 but up-regulates Phosphate transporters (PTs). Expression levels of csi-PHO2 (UGID: 1423690), csi-PT2 (UGID: 3374895), and csi-PHT2;1 (UGID: 2916608) relative to citrus actin were determined by quantitative real-time PCR (mean±SE). Total RNA from both 10- and 14-wpi samples (untreated and Las-treated) was used for reverse transcription followed by quantitative PCR. Expression level of untreated samples is assigned to 1. Experiments were repeated for 3 times with similar results. HLB: Las-infected; wpi: weeks post inoculation.
Figure 5:
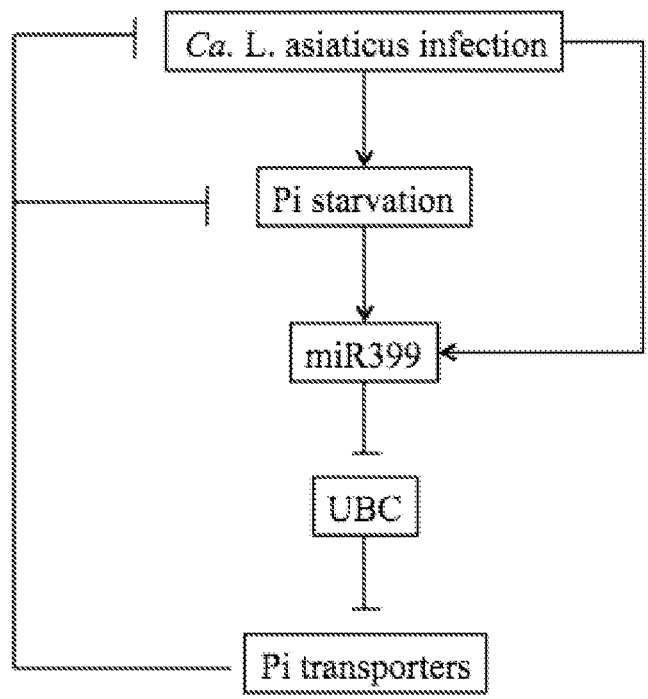
FIG. 5 shows the regulatory circuit mediated by miR399 in response to *Ca. L. asiaticus* infection.

We further tested our hypothesis by detecting PHO2 and PTs transcripts in both healthy and Las-infected plants by real-time PCR. After database searching, we identified one citrus PHO2 and two citrus PTs: csi.2677 (UGID: 1423690; homolog to *Arabidopsis* PHO2 [At2g33770; identity=69.9%]), csi.14938 (UGID: 3374895; homolog to AtPT2 [*Arabidopsis thaliana* phosphate transporter 2; AT2G38940; identity=85.2%]), and csi.9842 (UGID: 2916608; homolog to PHT2;1 [phosphate transporter 2;1; AT3G26570; identity=88.3%]). These citrus homologs therefore are referred as csi-PHO2, csi-PT2, and csi-PHT2;1 hereafter. We examined gene expression levels of PHO2 and PTs by real-time PCR. As shown in FIG. 4, we observed reduced csi-PHO2 expression level at both 10- and 14-wpi, agreeing with the increased miR399 expression at both time points, as well as the reduced Pi level; we also observed elevated expression of csi-PT2 and csi-PHT2;1, which are opposite to csi-PHO2 and in agreement with csi-PHO2's repressive role on csi-PTs. Taken together, our hypothesis was validated by the observation in concord with all the predictions: Pi-deficiency and induced miR399 in Las-infected plants, opposite expression profiles of csi-PHO2 (reduced) and csi-PT2 and -PHT2;1 (induced) at both time points of the Las-infected plants. Therefore, we propose that the miR399-PHO2 regulatory machinery is a conserved Pi homeostasis regulatory mechanism, at least between *Arabidopsis* and citrus.

Application of Inorganic Phosphorus Solution Largely Reduces HLB Symptoms

If Las infection leads to host Pi deficiency, which consequently caused observed symptoms such as yellowing, blotchy mottle, zinc-deficiency-like mottle, severe chlorosis, and most importantly, reduced fruit yield, then applying Pi to the infected plants should alleviate at least some of the HLB symptoms. We foliarly applied potassium poly phosphate (mono- and di-potassium salts of phosphorus acid 56%, plus potassium nitrate [$KNO_3$], and citrus spray oil) to Las-infected plants for two years. As controls, we also applied $KNO_3$ and citrus spray oil to infected plants, as well as untreated control trees that received no foliarly applied nutrients. After applying potassium poly phosphate for two years, the Las-infected plants showed dramatically reduced disease symptoms. Compared to untreated control trees and trees treated with nutrients only, the phosphate-treated trees have greener appearance, vigorous growth, and increased fruit yield. On the leaves from trees applied potassium poly phosphate, there is hardly any yellowing or blotchy mottle visible. In contrast, these symptoms are quite obvious on leaves from untreated trees or trees treated with nutrients only. The observed reduced symptoms are not due to application of potassium since the control plants also received KNO$_3$. Therefore, we conclude that applying Pi, but not potassium nutrients, to Las-infected citrus can relieve HLB symptoms. Our results indicate that Pi application may be employed for HLB management and restore fruit yield in infected regions.

Discussion

Citrus is an important economic plant globally, which is currently threatened by the very destructive citrus disease-HLB (Bove, 2006). One of the current challenges for HLB management is an effective HLB disease control reagent that can replace the costive eradication procedure, which is the only option currently available. Plants have evolved multiple levels of immune responses, including basal defense triggered by virulent pathogens in susceptible hosts and resistance (R) gene-mediated resistance activated by avirulent pathogens in resistant hosts (Chisholm et al., 2006; Jones & Dangl, 2006). Infection of bacterium *Ca. L.* in different genotypes of citrus plants causes different degrees of disease and symptoms. Although there is no known complete resistance in *Citrus* spp., tolerant citrus cultivars that have a very mild or no obvious disease symptom and with low bacterial titer were identified (Folimonova et al., 2009). Thus citrus hosts are capable of recognizing *Ca. L.* infection and responding to the pathogen in different degrees. The significance of this research is investigating the involvement of the citrus innate immune system in *Ca. L.* infection. Studying and understanding how citrus hosts use innate immunity as tools against *Ca. L.* should lead to utilizing of these innate immune tools as efficient biological reagents against *Ca. L.* in future. This is going to have a huge impact on the citrus industry considering HLB management-related cost is estimated about 40% higher than pre-HLB costs in the United states (Irey et al., 2008) and about 12.65-38.73% of the total operational costs in Sao Paulo, Brazil (Belasque et al., 2010).

Previous studies have shown that small RNAs are involved in basal defense and R gene-mediated resistance (Katiyar-Agarwal et al., 2006; Navarro et al., 2006; Katiyar-Agarwal et al., 2007; Zhang et al., 2011), as well as plant fitness adjusting mineral homeostasis (Jones-Rhoades & Bartel, 2004; Fujii et al., 2005; Burkhead et al., 2009). Our investigation of citrus small RNA populations revealed that citrus possess many conserved miRNAs, which can also be found in other plants, such as *Arabidopsis*. In most of the cases, bioinformatics analysis data agreed with our experimental very well. For example, there is a very good match between the bioinformatics prediction and experimental validation of the expression level of citrus conserved miRNAs; most of the miRNAs that were predicted more than 2-fold increase or decrease in both 10- and 14-wpi (FIG. 1) were successfully experimentally validated. This indicates that our bioinformatics approaches are not only powerful, but also reliable in investigating the dynamic small RNA populations upon pathogen challenge. Our results showed that some citrus miRNAs, such as miR 160, 396, 398, and 399, demonstrated distinguished expression patterns between healthy and Las-infected plants, among which miR399 and miR396 are the ones with potential practical value due to their relative high abundance.

Furthermore, the Las elicited miR399 induction and Pi deficiency suggests there might be connections between HLB and Pi level. Research has shown that in *Arabidopsis* the miR399/PHO2 regulatory machinery is turned on upon Pi starvation, and over-expression of miR399 induces accumulation of Pi (Fujii et al., 2005; Lin et al., 2008; Buhtz et al., 2010). Using public genomic DNA and expressed sequence tag data, Bari et al (2006) assembled potential orthologs of PHO2 from rice, *Medicago truncatula*, poplar, wheat (*Triticum aestivum*), soybean (*Glycine max*), cotton (*Gossypium hirsutum*), apple (*Malus domestica*), and orange (*Citrus aurantium*), but not in the *Physcomitrella patens* EST database or the genome sequences of *P. patens* and *C. reinhardtii*. These results suggest that the regulatory mechanism may be conserved across angiosperms and that it may have emerged during the evolution of higher plants.

If the citrus and *Arabidopsis* miR399 are really functionally conserved, as suggested by our data and observations by Bari et al (2006), this can be interpreted as that Las infection reduces host Pi level, which in turn triggered miR399 induction, as observed in this study. If this is true, then citrus miR399 should be induced upon Las infection, should participate in host Pi up-regulation pathways (by regulating PHO2 directly, and csi-PT2 and -PHT2;1 indirectly), and applying Pi should alleviate HLB symptoms.

Several lines of evidence support our hypothesis. First, as we demonstrated in this study, when citrus was affected by Las, Pi deficiency was observed (FIG. 4a), which is about >30% lower than in the healthy leaves. Some mineral nutrients, such as zinc and potassium, did not show noticeable variations. Second, citrus miR399 was specifically induced upon Las (FIG. 1), but not *S. citri* challenge. Although the overall expression level is relatively low in citrus, elevation in expression level could be detected unambiguously and consistently. Third, we proved that citrus miR399 is functionally conserved with its *Arabidopsis* homolog, which regulates Pi accumulation through down-regulating csi-PHO2 (FIG. 4). We also observed elevated expression of two Pi transporters-csi-PT2 and -PHT2;1, respectively. The cognate induction of citrus miR399, reduction on csi-PHO2 level, and induction of csi-PT2 and -PHT2;1 after Las infection suggests there is a functional miR399/PHO2/PTs pathway controlling Pi homeostasis, as being revealed in other species such as *Arabidopsis*, rapeseed, and pumpkin (Fujii et al., 2005; Buhtz et al., 2008; Pant et al., 2008). Fourth, field practice showed that when Pi is applied, HLB symptom is alleviated. This indicates that Las infection caused Pi deficiency contributes to observed HLB symptoms, including yellowing and reduced yields, and when normal Pi level is restored by applying Pi (or by endogenous mechanisms, such as the miR399 pathway), Las-infected citrus would show reduced symptom.

Based on our results, we propose a model in which citrus miR399 may play a role in citrus response to Las infection. In this model, Las infection causes a Pi deficiency on the host. This is consistent with current observation that Las is restricted to phloem, and Las infection usually cause phloem congestion (Folimonova & Achor, 2010). Reduced Pi level induces miR399 expression, which in turn down-regulates its target, csi-PHO2, a citrus ubiquitin conjugating enzyme. Based on its homology to *Arabidopsis* PHO2, csi-PHO2 may be a suppressor that restricts citrus phosphate transporter activity at normal conditions. Upon Las infection, the miR399-mediated reduction of csi-PHO2 consequently leads to induction of phosphate transporters, which recharge host cells' Pi reservoir. This model is similar to the model proposed in *Arabidopsis*, where mR399 and PHO2 play important roles in response to Pi deficiency (Lin et al., 2008). Foliar applying Pi to the Las-infected plants, which reduced HLB symptoms and enhanced fruit yield, validated our model. Our model may explain the filed practice that applying nutrition to infected tree can maintain tree health and productivity. Studies showed that *Ca. L.* infection restricted either nutrient uptake or transport and that foliar applied minerals could prolong tree life and reduce yield losses (Pustika et al., 2008).

Our model does not exclude the possibility that miR399 can be directly induced by Las infection. Research has shown that miR393 and miR393b* can be induced by bacterial pathogens, and their induction contributes to antibacterial resistance (Navarro et al., 2006; Zhang et al., 2011). We speculate that over-expression of miR399 in Las-infected citrus should reduce HLB symptoms. Whether normal or enhanced Pi level in citrus plants have an inhibitory effect on infection and/or propagation of Las in hosts remains to be investigated in future. It should be noted that besides phosphorus, we also observed reduced iron level after Las infection (FIG. 4*a*). It seems that after Las infection, the congested phloem also affects homeostasis of other mineral elements.

This example demonstrates the *Ca. L. asiaticus* infection of citrus plants can be detected by detecting the expression of miRNAs and siRNAs, and that HLB disease symptoms can be ameliorated by treatment of plants with phosphorous.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method for detecting the level of expression of one or more RNA in a sample from a citrus plant, the method comprising detecting a miRNA399 RNA in the sample by
   (i) contacting a sample from a citrus plant suspected of being infected with HLB disease or having a *Ca. L. asiaticus*-infection with a nucleic acid that specifically hybridizes to the RNA,
   (ii) contacting a sample from a citrus plant that is not infected with HLB disease or does not have a *Ca. L. asiaticus*-infection with a nucleic acid that specifically hybridizes to the RNA,
   detecting increased expression of the miRNA399 RNA in the sample from the citrus plant suspected of being infected with HLB disease by a method selected from Northern analysis, polymerase chain reaction (PCR), reverse-transcription-PCR (RT-PCR), or hydrizing the RNA to a microarray, and
   contacting the citrus plant suspected of being infected with HLB disease with phosphate or a phosphorus oxyanion;
   wherein the miRNA399 comprises a sequence selected from UGCCAAAGGAGAUUUGCCCGG (SEQ ID NO:9), UGCCAAAGGAGAGUUGCCCUA (SEQ ID NO:10), UGCCAAAGGAGAAUUGCCCUG (SEQ ID NO:11), or UGCCAAAGGAGAGUUGCCCUG (SEQ ID NO:12).

2. The method of claim 1, further comprising detecting an RNA selected from the group consisting of siRNA1005, siRNA1008 and siRNA1009 in the sample from (i), wherein
   the siRNA1005 comprises a sequence at least 90% identical to ATAGATAATGGATCAACGGTTATA (SEQ ID NO:13);
   the siRNA1008 comprises a sequence at least 90% identical to TCGAACAAGGTAAGGATGTCA (SEQ ID NO:14) or CCTTGTTCGAACAAGGTAAGGATGTCATTCTTT (SEQ ID NO:100); and
   the siRNA1009 comprises a sequence at least 90% identical to CTTCTAATAAACATGCATGAA (SEQ ID NO:15) or CGTCTTCTAATAAACATGCATGAACTTATT (SEQ ID NO:101).

3. The method of claim 1, wherein the method further comprises detecting the mRNA of a ubiquitin-conjugating enzyme E2 (UBC) gene.

4. The method of claim 3, wherein the UBC mRNA comprises a sequence that is at least 90% identical to SEQ ID NO:84.

5. The method of claim 1, wherein the method further comprises measuring phosphate levels in the plant.

6. The method of claim 1, wherein the nucleic acid is labeled with a detectable probe.

7. The method of claim 1, wherein the detecting is performed using a nucleic acid dipstick.

* * * * *